United States Patent
Tunius

(10) Patent No.: US 10,703,942 B2
(45) Date of Patent: Jul. 7, 2020

(54) LOW CYTOTOXICITY SWITCHABLE ADHESIVE COMPOSITIONS, MEDICAL DRESSINGS AND SKIN COVERINGS, AND METHODS OF TREATMENT USING SAME

(71) Applicant: Lumina Adhesives AB, Gothenburg (SE)

(72) Inventor: Mats Tunius, Gothenburg (SE)

(73) Assignee: LUMINA ADHESIVES AB, Gothenburg (SE)

( * ) Notice: Subject to any disclaimer, the term of this patent is extended or adjusted under 35 U.S.C. 154(b) by 900 days.

(21) Appl. No.: 15/119,685

(22) PCT Filed: Mar. 5, 2015

(86) PCT No.: PCT/GB2015/000079
§ 371 (c)(1),
(2) Date: Aug. 17, 2016

(87) PCT Pub. No.: WO2015/132551
PCT Pub. Date: Sep. 11, 2015

(65) Prior Publication Data
US 2017/0051189 A1 Feb. 23, 2017

(30) Foreign Application Priority Data
Mar. 5, 2014 (GB) .................................. 1404021.6

(51) Int. Cl.
| | | |
|---|---|---|
| C08F 2/46 | (2006.01) | |
| C08F 2/50 | (2006.01) | |
| C08G 61/04 | (2006.01) | |
| C09J 133/14 | (2006.01) | |
| C09J 4/06 | (2006.01) | |
| C08F 220/10 | (2006.01) | |
| C08F 220/06 | (2006.01) | |
| A61B 46/20 | (2016.01) | |
| A61F 13/02 | (2006.01) | |
| A61L 15/58 | (2006.01) | |
| A61L 31/04 | (2006.01) | |
| A61L 31/14 | (2006.01) | |
| C08F 222/10 | (2006.01) | |

(52) U.S. Cl.
CPC .............. *C09J 133/14* (2013.01); *A61B 46/20* (2016.02); *A61F 13/023* (2013.01); *A61F 13/0206* (2013.01); *A61F 13/0253* (2013.01); *A61F 13/0266* (2013.01); *A61L 15/585* (2013.01); *A61L 31/041* (2013.01); *A61L 31/14* (2013.01); *C08F 220/06* (2013.01); *C08F 220/10* (2013.01); *C09J 4/06* (2013.01); *A61B 2046/205* (2016.02); *C08F 222/1065* (2020.02)

(58) Field of Classification Search
CPC . C09J 133/14; A61F 13/0253; A61F 13/0266; A61F 13/0206; A61L 31/14; A61L 31/041; A61L 15/585; A61B 2046/205
USPC .................... 522/7, 6, 189, 184, 71, 1; 520/1
See application file for complete search history.

(56) References Cited

U.S. PATENT DOCUMENTS

| | | | |
|---|---|---|---|
| 2004/0077882 A1 | 4/2004 | Moszner et al. | |
| 2011/0206869 A1 | 8/2011 | Nemoto et al. | |
| 2013/0017246 A1* | 1/2013 | Tunius | ..... A61F 13/02 |
| | | | 424/445 |
| 2013/0068386 A1 | 3/2013 | Lack et al. | |
| 2018/0030321 A1* | 2/2018 | Tunius | ..... C08G 18/4829 |

FOREIGN PATENT DOCUMENTS

| | | | |
|---|---|---|---|
| CN | 102533184 | 7/2012 | |
| EP | 2371920 | 10/2011 | |
| WO | 9706836 | 2/1997 | |
| WO | 9938900 | 8/1999 | |
| WO | 2005090509 | 9/2005 | |
| WO | 2005105857 | 11/2005 | |
| WO | 2010034998 | 4/2010 | |
| WO | WO-2011121303 A1 * | 10/2011 | ............. A61F 13/02 |

OTHER PUBLICATIONS

International Search Report dated Jun. 5, 2015.
United Kingdom Search Report dated Sep. 2, 2014.

* cited by examiner

*Primary Examiner* — Jessica Whiteley
(74) *Attorney, Agent, or Firm* — Lowenstein Sandler LLP

(57) ABSTRACT

Low cytotoxicity compositions are disclosed, most particularly for use in adhesive medical products such as wound dressings (100) and medical skin coverings including surgical incision drapes, bacterial barriers without a wound pad for covering wounds and skin closure products. Methods of treatment are also disclosed that use the adhesive medical products, for example on patients with an injury or a long-term medical condition requiring repeated application of dressings, on patients undergoing surgery, on patients after surgery and/or injury requiring a skin covering, and skin closure methods.

38 Claims, 12 Drawing Sheets

LOW CYTOTOXICITY SWITCHABLE ADHESIVE COMPOSITIONS, MEDICAL DRESSINGS AND SKIN COVERINGS, AND METHODS OF TREATMENT USING SAME

CROSS-REFERENCE TO RELATED APPLICATIONS

This application is a national stage entry under 35 U.S.C. § 371 of International Application No. PCT/GB2015/00079, filed Mar. 5, 2015, which claims the benefit of priority of GB Application No. 1404021.6, filed Mar. 5, 2014, the disclosures of which are hereby incorporated by reference herein in their entirety.

The present invention relates to low cytotoxicity compositions, most particularly for use in adhesive medical products such as wound dressings and medical skin coverings including surgical incision drapes, bacterial barriers for covering wounds (without a wound pad) and skin closure devices. The invention also relates to methods of treatment using these products on patients with an injury or a long-term medical condition requiring repeated application of dressings, on patients undergoing surgery, on patients after surgery and/or injury requiring a skin covering, and for skin closure applications.

The medical skin coverings mentioned above have in common the feature that they are applied to the skin at a site where a break in the skin surface has occurred, for example cuts, scratches and/or abrasions, or at a site where a break in the skin surface will be made by surgery.

Adhesive medical skin coverings, such as adhesive surgical medical dressings and adhesive bandages normally comprise a layer of pressure sensitive adhesive. However, when a conventional adhesive dressing and/or adhesive bandage is removed from a patient's skin, it can often cause localised trauma and/or pain to the patient. This is particularly true for patients with long-term conditions that require an adhesive dressing to be applied to the same part of the body repeatedly over a prolonged period, such as stoma patients. It is also true for patients with fragile skin, especially the elderly and young children.

In order to address this problem, the applicants have developed pressure sensitive adhesive compositions that are rapidly "switchable" from a tacky state to a non-tacky or low-tack state upon exposure to visible light or UV radiation such that the switched adhesive composition has a reduced peel strength compared to its unswitched state. Adhesive dressings prepared using a switchable pressure sensitive adhesive composition of the above type are described in published international patent application No. WO 2010/034998 A1.

There are a number of known pressure sensitive adhesives that are approved for use with medical skin coverings but, unlike the adhesive compositions described in WO 2010/034998 A1, these known pressure sensitive adhesives approved for use with medical skin coverings are not switchable from a tacky state to a non-tacky or low-tack state.

In circumstances in which the medical skin covering will be in contact with a patient's skin for a prolonged period, or in which the medical skin covering will be replaced with a new medical skin covering several times over a prolonged period, it is particularly important for the switchable adhesive compositions that are used in the medical skin coverings to be of low cytotoxicity. Whilst an approved pressure sensitive adhesive can be selected for the adhesive component of such a switchable adhesive composition, the other constituents in the switchable adhesive composition must also be of low cytotoxicity for applications in which the medical skin covering will be in contact with the patient's skin for a prolonged period, or in applications in which the medical skin covering will be replaced with a new medical skin covering several times over a prolonged period.

The present invention has been made in view of the above problem.

The invention provides a switchable adhesive composition comprising a mixture of a pressure sensitive adhesive component, curable molecules that are curable by free radical polymerization, a photoinitiator, and a stabiliser, wherein the curable molecules are oligomers of at least one of the following formulae (I) to (VII):

where n is 0 or an integer from 1 to 100,
A is a diisocyanate, a diepoxide, a diol or a dicarboxylic acid;
B is a diol when A is a diisocyanate or a dicarboxylic acid; B is a dicarboxylic acid when A is a diepoxide or a diol;
C is a hydroxyl containing double bond carrying molecule when A is a diisocyanate or a dicarboxylic acid; C is a carboxylic acid double bond carrying molecule when A is a diepoxide or a diol;

where n is 0 or an integer from 1 to 100,
E is a tri-isocyanate, a triepoxide, a triol or a tricarboxylic acid;
B is a diol when E is a tri-isocyanate or a tricarboxylic acid; B is a dicarboxylic acid when E is a triepoxide or a triol;
C is a hydroxyl containing double bond carrying molecule when E is a tri-isocyanate or a tricarboxylic acid; C is a carboxylic acid double bond carrying molecule when E is a triepoxide or a triol;

where n is 0 or an integer from 1 to 100,
E is a tri-isocyanate, a triepoxide, a triol or a tricarboxylic acid;
F is a triol when E is a tri-isocyanate or a tricarboxylic acid; F is a tricarboxylic acid when E is a triepoxide or a triol;
C is a hydroxyl containing double bond carrying molecule when E is a tri-isocyanate or a tricarboxylic acid; C is a carboxylic acid double bond carrying molecule when E is a triepoxide or a triol;

where n is 0 or an integer from 1 to 100,
G is a tetra-isocyanate, a tetra-epoxide, a tetra-ol or a tetra-carboxylic acid;
B is a diol when G is a tetra-isocyanate or a tetra-carboxylic acid; B is a dicarboxylic acid when G is a tetra-epoxide or a tetra-ol;
C is a hydroxyl containing double bond carrying molecule when G is a tetra-isocyanate or a tetra-carboxylic acid; C is a carboxylic acid double bond carrying molecule when G is a tetra-epoxide or a tetra-ol;

where D is a symmetrical isocyanurate trimeric ring structure or an asymmetric trimeric iminooxadiazinedione ring structure consisting of three diisocyanate molecules, or a linear trimeric biuret or allophanate structure, C is a hydroxyl containing double bond carrying molecule;

 (VII)

where x is 1, 2, 3, 4, 5 or 6,
$H_x$ is x symmetrical isocyanurate trimeric ring structures or x asymmetric trimeric iminooxadiazinedione ring structures consisting of three diisocyanate molecules, or x linear trimeric biuret or allophanate structures linked together in a homopolymer,
C is a hydroxyl containing double bond carrying molecule;

 (VII)

where y is 2, 3, 4, 5, 6, 7, 8, or 9,
$I_y$ is polyisocyanate, a polyepoxide, a polyol or a polycarboxylic acid with y numbers of functionalities;
C is a hydroxyl containing double bond carrying molecule when I is an polyisocyanate or a polycarboxylic acid; C is a carboxylic acid double bond carrying molecule when I is a polyepoxide or a polyol;
and wherein the oligomers have a weight average molecular weight in the range from 500 to 10,000 dalton.

In the case of formula (I), $CA(BA)_nC$, the component C may be a hydroxyl containing acrylate ester when A is a diisocyanate or a dicarboxylic acid, or C may be an acrylic acid when A is a diepoxide or a diol.

In the case of formula (II), $C_2E(BCE)_nC$, the component C may be a hydroxyl containing acrylate ester when E is a tri-isocyanate or a hicarboxylic acid, or C may be an acrylic acid when E is a triepoxide or a triol.

In the case of formula (III), $E_{(2n+1)}F_nC_{(3n+3)}$, the component C may be a hydroxyl containing acrylate ester when E is a tri-isocyanate or a tricarboxylic acid, or C may be an acrylic acid when E is a triepoxide or a triol.

In the case of formula (IV), $G_{(n+1)}B_nC_{(2n+4)}$, the component C may be a hydroxyl containing acrylate ester when G is a tetra-isocyanate or a tetra-carboxylic acid, or C may be a dicarboxylic acid when G is a tetra-epoxide or a tetra-ol.

In the case of formula (V), $DC_3$, the component C may be a hydroxyl containing acrylate ester.

In the case of formula (VI), $H_xC_{(x+2)}$, the component C may be a hydroxyl containing acrylate ester.

In the case of formula (VII), $I_yC_y$, the component C may be a hydroxyl containing acrylate ester when I is a polyisocyanate or a polycarboxylic acid, or C may be an acrylic acid when I is a polyepoxide or a polyol.

For the avoidance of doubt, references in the preceding paragraphs to "acrylic esters" and "acrylic acids" include methacrylic esters and methacrylic acids.

A major advantage of the switchable adhesive compositions according to the present invention compared with known medical adhesives is that biocompatible switchable medical adhesives exhibiting a zero in cytotoxicity tests complying with the methods described in ISO 10993-5 standard for the eluation test and also complying with the United States Pharmacopeia: <87> Biological Reactivity Tests, in vitro (Eluation Test) can be produced in an ample variation.

Another advantage is that medium range molecular weight residuals (150-450 dalton or, in some cases, 150-900 dalton) in the produced adhesive composition can be kept at very low concentrations. This is important because larger molecules are not able to penetrate the skin easily. Generally, skin penetration is believed to occur below around 500-1000 dalton, depending on the chemical nature of the molecule. For example, low polarity organic molecules may penetrate skin because their transport through skin is aided by skin grease (sebum).

Another advantage is that the oligomeric curable molecules can be tailored to optimize the final switchable adhesive compositions for properties such as moisture vapour transmission rate (MVTR), viscosity, switching performance, adhesion, hydrophobic/hydrophilic balance, migration into and wrinkling of medical carrier films, etc.

Oligomeric Curable Molecule Structure

Oligomers for use as the curable molecules in switchable adhesive compositions in accordance with the present invention consist of a backbone molecule such as a polyether, a polyester, a polyurethane, a homopolymer of isocyanate, etc., with attached double bond-containing groups.

The first step in synthesizing such an oligomer is to produce the backbone molecule (if a suitable candidate cannot be obtained from commercial sources) with pendant groups such as hydroxyl, epoxide, carboxylic acid, isocyanate, etc., so that the double bond-containing molecule can be chemically bonded to the backbone molecule in a later stage. In general, any double bond-containing molecule having a suitable function in order to be attached to the backbone molecule could be used to form the pendant groups, but preferred species are hydroxyl containing acrylic esters and acrylic acids or hydroxyl containing methacrylic esters and methacrylic acids.

Preferred examples of chemical reactions that can be used to attach the double bond-containing molecules to the backbone molecules are reactions between epoxides and acrylic acids, hydroxyl and acrylic acids, transesterfication of acrylic acid to hydroxyl groups, isocyanate and hydroxyl containing acrylic esters. The most preferred of these examples is the reaction between isocyanate and hydroxyl containing acrylic esters.

In principle, each of the needed reactive functions can be situated either on the backbone molecule or on the double bond-containing molecule but, most commonly, epoxides and isocyanate functions are provided on the backbone molecule, while the hydroxyl function is usually attached to the backbone molecule in the case of an ester forming reaction or is usually attached on the double bond-containing molecule in the case of a urethane forming reaction.

Oligomer Specifications

Residuals of molecules below 450 dalton or more preferably 900 dalton should be kept at concentrations below 3 w/w % or more preferably below 1 w/w %. This ensures that the number of low molecular weight species is minimised. It does not necessarily apply to residual molecules of less than approximately 200 dalton because these will generally be evaporated during drying steps in the manufacturing process when the switchable adhesive composition is coated on a substrate and dried at elevated temperature.

Preferred is methacrylic acid or its related hydroxyl-containing esters, since methacrylated oligomers are in general less toxic and less allergenic than their acrylate counterparts.

Preferred hydroxyl-containing acrylic esters are hydroxyl ethylmethacrylate or propoxylated methacrylic acid esters containing 1-6 propylene glycol units alternatively their ethylene glycol counterparts can be used but this is usually less beneficial when more than 2 ethylene glycol units (n<3) are used due to that they contribute to a more hydrophilic, slightly lower molecular weight and higher viscosity of the oligomer.

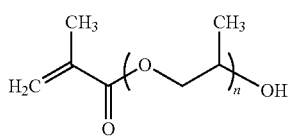

where n is 1-6

Examples of other hydroxyl containing acrylic esters are hydroxyl (CH2)n methacrylic esters where n is 4-8, caprolactone methacrylate, and 3-(Acryloyloxy)-2-hydroxypropyl methacrylate.

In order to produce an adhesive with satisfactory switching performance (reduction in peel force, switching time), the pure oligomer should contain at least 1 equivalent of double bonds per kg (mol/kg) but preferred are oligomers with more than 2 double bond equivalents per kg.

To avoid migration into and swelling of common medical polymeric films used as carrier films or release layers, the oligomer needs to have a weight average molecular weight, Mw, of at least 500 dalton, more preferably at least 1500 dalton, combined with a very low amount of molecules below 400 dalton or more preferably below 900. Preferably, the hydrophobic/hydrophilic balance of the oligomer should be different from that of the medical polymeric film.

It is preferred that the oligomer has an average number of curable functions per molecule of 2 or more. Multiple functionalities of 2 or more, for example 3 or more, or functionalities of 4 or more, are especially effective because oligomeric curable molecules of this type are able to form highly cross-linked three-dimensional polymeric networks which are an important feature in transforming the adhesive compositions of the invention from a tacky state to a non-tacky or low-tack state and from a viscoelastic state to an elastic state.

If the Mw of the oligomer is increased, it is important to increase the number of curable functions per molecule in order to conserve the equivalent number of double bonds per kg.

In order to ensure low cytotoxicity, it is important to avoid oligomers that are too hydrophilic because they may be soluble in water to some degree and will therefore behave as more toxic towards the living cells used in the cytotoxicity test.

Preferred isocyanates are trimethyl hexamethylene diisocyanate, dicyclohexylmethane-4,4'-diisocyanate, isophorone diisocyanate, toluylene diisocyanate while more preferred are homopolymers of diisocyanate, e.g., allophanates, isocyanurates, iminooxadiazindiones, and biurets based on diisocyanates such as hexamethylene diisocyanate and isophorone diisocyanate.

Methods for Controlling Different Parameters

Moisture Vapour Transmission Rate (MVTR)

The moisture breathability of the adhesive composition can be improved by using more hydrophilic building blocks in the oligomer, e.g., by partly or completely exchanging diols such as polypropylene glycol or butanediol with polyethylene glycol. Similarly, hydroxyl containing esters such as mono or polypropylene glycol monomethacrylate can be partly or completely exchanged with mono or poly ethylene glycol methacrylate.

Switching Performance

The reactivity of the composition can be increased by using a higher number of curable groups/molecule in the oligomer and/or by using more reactive functionalities in the oligomer, e.g., partly or completely exchanging methacrylate with acrylate (acrylates are more reactive but also slightly more toxic) and/or by using a higher proportion of oligomeric curable molecules in the adhesive composition Viscosity of the Pure Oligomer The interactions between oligomer molecules and thereby the viscosity of the oligomer can be decreased by using bulky groups (e.g., by adding methyl groups or by branching of the molecular chain) and/or introducing asymmetry or higher hydrophobicity in the oligomer molecules e.g., by exchanging hexamethylene diisocyanate with trimethylhexamethylene diisocyanate, exchanging isocyanurate with iminooxadiazinedione, exchanging butanediol with methylpentandiol, exchanging polyethylene glycol with polypropylene glycol, etc.

Adhesion

This parameter can be regulated by the polarity or viscoelastic properties of the oligomer.

Hydrophobic/Hydrophilic Balance

See MVTR.

Migration

Diffusion of the oligomer into the medical film used as a carrier layer or release liner is governed by the size of the molecules and their solubility in the films.

Examples of Backbone Molecules with Suitable Pendant Functions

Polyethers are usually propoxylated/ethoxylated bisphenol A, alkyl diol, alkyltriol, as well as mono-, di- or higher trimethylolpropane or pentaerythritol.

Polyesters end capped with hydroxyl groups are produced by reacting dicarboxylic acids with a slight excess of a diol. If a higher number than 2 acrylate functions is needed, polyols like trimethylolpropane or pentaerythritol could be included as well as curable unsaturated diacids such as itaconic, fumaric and maleic acid.

Backbone molecules with pendant epoxy groups can be produced, for example, by reacting an excess of di-epoxides with saturated or unsaturated diacids (in a similar fashion to diol and diisocyanate to result in the products A, ABA, ABABA etc).

Adhesive Compositions

The invention may use an adhesive composition comprising a mixture, in proportions by weight, of 10% to 95% of a pressure sensitive adhesive constituent, 10% to 85% of oligomeric curable molecules that are curable by free radical polymerization, 0.1% to 10% of photoinitiator, and 0.01% to 2% of stabiliser, the balance being incidental constituents. Preferably, the pressure sensitive adhesive component and the curable molecules are mutually soluble when dry, although good results are obtained when the curable molecules are uniformly dispersed in the adhesive component, said adhesive component and curable molecules being mutually insoluble or only partly mutually soluble when dry.

Preferably, the amount of pressure sensitive adhesive component present in the mixture is in the range 20% to 75% by weight, more preferably 40% to 70% by weight. Preferably, the proportion of oligomeric curable molecules in the mixture ranges from 20% to 75% by weight, more preferably 30% to 60% by weight. Preferably, the photoinitiator is present in the mixture in the proportions 0.1% to 5% by weight, more preferably 0.5% to 2% by weight. Preferably, the photoinitiator is also soluble in the dry mixture of pressure sensitive adhesive component and oligomeric curable molecules, although it will be capable of exerting its curing initiating effect upon exposure to an activating light source if finely dispersed through the dry mixture but not dissolved in it.

The adhesive mixture also contains a stabiliser which is added in order to prevent spontaneous reaction of the curable molecules during storage.

The weight proportion for the pressure sensitive adhesive component is given above in terms of its dry weight and excludes any solvent which might normally be present in a commercially available bulk adhesive product.

The composition may also include a polymer cross-linker that is cross-linkable by a mechanism other than free radical polymerization, for cross linking the pressure sensitive adhesive component. The internal cross-linker may be included, for example, for applications in which the cohesive strength of the adhesive composition (before the curable molecules are cured) is important. An example of such an application would be for skin closure, where an adhesive composition with low cohesive strength may be inadequate to hold the skin edges together while the curable molecules undergo their free radical curing upon exposure to UV light or visible light. In these circumstances, a polymer cross-linker in the adhesive component increases the cohesive strength of the composition and enables the composition to hold the skin edges together while the curable molecules undergo curing.

In certain embodiments, the weight proportion of the pressure sensitive adhesive component is from one of the following lower endpoints (inclusive), or from one of the following upper endpoints (inclusive). The lower endpoints are 10%, 20%, 30%, 40%, 50%, 60% and 70%; the upper endpoints are 95%, 90%, 85%, 80% and 75%. In certain embodiments, the weight proportion of curable molecules is from one of the following lower endpoints (inclusive), or from one of the following upper endpoints (inclusive). The lower endpoints are 10%, 20% and 25%; the upper endpoints are 85%, 80%, 70%, 60%, 50%, 40% and 30%. In certain embodiments, the weight proportion of photoinitiator is from one of the following lower endpoints (inclusive), or from one of the following upper endpoints (inclusive). The lower endpoints are 0.1%, 0.2%, 0.5% and 1.0%; the upper endpoints are 10%, 5%, 4% and 3%.

The incidental constituents may be one or more of light scattering particles, fungicides, bactericides, colorants, humectants, tackifiers, etc.

Adhesive Composition Preparation Method

The preparation method for the adhesive compositions used in the invention is very simple. The pressure sensitive adhesive component, the oligomeric curable molecules, the photoinitiator and stabiliser are stirred together, in darkness or under red light conditions if a visible light photoinitiator is used or in absence of UV light if a UV photoinitiator is used, for about 30 to 60 minutes, most conveniently at room temperature. The pressure sensitive adhesive component is usually supplied in solution (typically, 40% to 60% solids by weight); the curable molecules are usually solvent free, although some curable molecules of high viscosity may be carried in a solvent; the photoinitiator is usually solid and the most difficult component of the system to dissolve and/or disperse.

Following completion of the stirring together, the resulting solution is coated at a certain thickness onto a carrier film—typically about 100 µm when wet—and then left to dry at room temperature for about 10 minutes.

The spread adhesive mixture is then further dried at 80-150° C. for 3 to 10 minutes. A slightly higher temperature and a longer drying time can be used if necessary. After drying, the thickness of the spread adhesive mixture will typically be about 60 µm.

A second carrier film is then applied to the other surface of the adhesive mixture. Preferably, one of the carrier films has a lower release force compared to the other. A difference in release force helps to enable the adhesive composition to remain in place on one of the carrier films whilst the other carrier film is removed so that the thus-exposed adhesive can be applied to skin. Differences in release force may be achieved, for example, by having one of the films siliconised or by using carrier films of different surface roughness; the adhesive composition will stick preferentially to the carrier film with greater surface roughness.

If it is intended that the adhesive composition should be easily removed from the skin after switching, the surface of the carrier film may be left untreated. On the other hand, if it is intended that the adhesive composition should remain on the skin after curing of the curable molecules in the adhesive composition, the surface of the carrier film next to the adhesive composition layer is treated with a coating of a silicone release agent. As a result, the carrier films have a low surface energy. By contrast, skin is not smooth (at a microscopic level) and has many surface irregularities, including pores. Hence, skin has an inherently high surface area as well as a high surface energy compared to the siliconised carrier films. Typical release forces for carrier films that are to be used as release liners when it is intended that the adhesive composition should remain on the skin after switching are given below, measured using Final test method no. 10 and TESA 7475 tape of 25 mm width:

| Release liner | Release levels (cN/25 mm) | Preferred range of release levels (cN/25 mm) |
| --- | --- | --- |
| 1st (removed prior to skin application) | 1-50 | 1-15 |
| 2nd to be removed after curing | 15-2000 | 50-100 |

Carrier Film

Exemplary materials for the carrier film for carrying the switchable adhesive composition layer include polyethylene, polypropylene, polyurethane, ethylene/propylene copolymers, ethylene/ethylacrylate copolymers, ethylene/vinyl acetate copolymers, silicone elastomers, polydimethylsiloxanes, neoprene rubber, polyisobutylene, polyacrylates, chlorinated poly-ethylene, polyvinyl chloride, vinyl chloride-vinyl acetate copolymer, crosslinked polymethacrylate polymers (hydrogel), polyvinylidene chloride, poly (ethylene terephthalate), butyl rubber, epichlorohydrin rubbers, ethylenevinyl alcohol copolymers, ethylene-vinyloxyethanol copolymers; silicone copolymers, for example, polysiloxane-polycarbonate copolymers, polysiloxanepolyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxy propyl methyl cellulose, and cellulose esters; polycarbonates; polytetrafluoro-ethylene; and the like. More preferred are medical grade polyether or polyester polyurethanes, thermoplastic polyester elastomer, perforated polyethylene, polypropylene and PET films, as well as medical grade woven or non woven materials.

Photoinitiator

The photoinitiator may be any species which is capable of producing radical species under mild conditions, e.g., long wavelength UV (UVA, e.g., 315-400 nm) or visible light, in order to promote radical polymerization reactions in the curable molecules. As a consequence, when the photoinitiator becomes activated by exposure to long wavelength UV or visible light, the oligomeric curable molecules form chemical bonds with other oligomeric curable molecules and hence create polymeric cross-linking. One effect of such cross-linking is to build a three-dimensional polymeric network entangling the pressure sensitive adhesive polymer chains, thereby reducing their mobility and free volume. Curable molecules having multiple functionality are able to form highly cross-linked three-dimensional polymeric networks easily. Another effect of the cross-linking is that the relative low molecular weight oligomer acts as a plasticiser on the adhesive component, increasing its tackiness and viscosity before switch, but not afterwards.

Preferably, for the medical applications described here, the UV exposure is under the mild conditions of long wave UV. The photoinitiator may alternatively produce radical species upon exposure to visible light, but products that are curable upon exposure to visible light require careful handling and/or require additional visible light occlusive layers to be incorporated in the product to avoid premature switching of the adhesive. The visible light occlusive layers need to be removed from the product at the appropriate time, when switching is desired.

Stabiliser

The switchable adhesive composition mixture also contains a stabiliser which is added in order to prevent spontaneous reaction of the curable molecules during storage. Examples of such stabilisers are hydroquinones such as Methoxy phenol (sometimes referred to as hydroquinone monomethyl ether), or 1-Piperidinyloxy-4,4'-[1,10-dioxo-1,10-decanediyl) bis (oxy)] bis [2,2,6,6-tetra methyl] and Pentaerythritol tetrakis(3-(3,5-di-tert-butyl-4-hydroxyphenyl)propionate).

Optional Constituents

The switchable adhesive composition may also include photo-sensitisers. Since a sensitising species often absorbs energy in a different part of the spectrum from the initiator, more effective use of the light source may be achievable through the incorporation of sensitisers into the mixture. Many photo-sensitisers are complex organic molecules, absorbing in the long wavelength UV and/or visible portion of the spectrum.

The switchable adhesive composition may also incorporate scattering particles to increase the effect of irradiation of the adhesive mixture by scattering the irradiating UV or visible light through the thickness of the adhesive mixture. Preferably, the light scattering particles are an inorganic compound such as silica powder, alumina powder, silica-alumina powder or mica powder with particle sizes of the order of 10 nm or greater, typically up to 1 µm.

Any conventionally known free radical initiators may be used. Particularly preferred are those initiators which react to long wavelength UV radiation, although initiators which react under visible light may be used. Thus, suitable free radical initiators include benzoin ethyl ether, ethanone, 1-[9-ethyl-6-(2-methylbenzoyl)-9H-carbazol-3-yl]-1-(o-acetyloxime), 2-benzyl-2-dimethylamino-1-(4-morpholinophenyl)-butanone-1, bis(2,4,6-trimethylbenzoyl)-phenylphosphineoxide, 2,4,6-trimethyl benzoyldiphenylphosphine oxide, 2-ethylanthraquinone, 2-methyl-1[4-(methylthio)phenyl]-2-morpholinopropan-1-one, as well as the visible light sensitive titanocene photoinitiators; dye/co-initiator systems, e.g., thionine/triethanol-amine; dye/borate salt systems; dye/peroxide systems and thioxanthone/tertiary amine system e.g. isopropylthioxanthone/quinone/tertiary amine and 1,2-diketone/co-initiator systems, e.g., camphor-quinone/tertiary amine.

Examples of suitable photoinitiators for use in an adhesive medical skin covering are: benzoin, ethyl benzoin, isopropyl benzoin, 2,4,6-trimethylbenzoyl diphenylphosphine oxide, 2-Benzyl-2-dimethylamino-1-(4-morpholinophenyl)-butanone-1, 2-Hydroxy-2-methyl-1-phenyl-propan-1-one, Bis(2,4,6-trimethyl benzoyl)-phenylphosphineoxide, 2-Methyl-1 [4-(methylthio)phenyl]-2-morpholino-propan-1-one, 1[9-ethyl-6-(2-methylbenzoyl)-9H-carbazol-3-yl]-, 1-(O-acetyloxime), 2-Hydroxy-1-{4-[4-(2-hydroxy-2-methyl-propionyl)-benzyl]-phenyl}-2-methyl-propan-1-one, 4,4'-bis(diethylamino)benzophenone, 2-chlorothioxanthen-9-one, 4-(dimethylamino)benzophenone, 2,5-dimethylbenzophenone, 4-hydroxybenzophenene, methylbenzoylformate, Phenanthrenequinone, 2-ethylanthraquinone, Bis(.eta.5-2,4-cylcopentadien-1-yl)-bis(2,6-difluoro-3-(1H-pyrrol-1-yl)-phenyl) titanium; Bis(2,4,6-trimethyl-benzoyl)-phenylphosphineoxide; camphor-quinone in combination with a tertiary amine; 2,4-Diethylthioxanthone in combination with a tertiary amine, and Isopropylthioxanthone combined with a tertiary amine.

Preferred visible light free radical photoinitiators are the titanocene initiators such as bis.(eta.5-cyclopentadienyl)-bis (2,6-difluoro-3-[pyrrol-1-yl]-phenyl) titanium, sold in the UK by Ciba Geigy as Irgacure 784 (Trade Mark).

The switchable adhesive composition may also include a component containing aliphatic thiol groups for reducing oxygen inhibition of the radical polymerization at the surface and preventing the surface from remaining tacky after cure when the surface is not protected by a film (second release liner). Apart from having oxygen-scavenging properties the aliphatic thiols can also take part in the radical polymerization of the curable molecules via thiol-ene reactions. For more effective contribution to the curing reaction a component with two or more thiol groups could be used, such as trimethylolpropanetris(3-mercaptopropionate) or pentaerythritoltetrakis(2-mercapto acetate). Amine synergists such as triethanol amine, ethyl-4-dimethylaminobenzoate or acrylated amines could also be used to reduce oxygen inhibition of the radical polymerization at the adhesive surface when this is not protected by a film.

Adhesive Wound Dressings

Adhesive wound dressings usually consist of an absorbent pad for absorbing exudates from the dressed wound, the absorbent pad being surrounded by an adhesive area for securing the wound pad in position over the wound. The adhesive area and the wound pad are supported on a carrier film which is often flesh coloured or of which may sometimes have an attractive design on its visible surface. The switchable adhesive compositions according to the present invention are ideal candidates for use as the adhesive in the adhesive area around the wound pad of an adhesive wound dressing.

Adhesive wound dressings are often applied by lay users in their own homes and are not necessarily apply by trained medical practitioners. Since few homes have access to suitable UV irradiation equipment, adhesive wound dressings incorporating the switchable adhesive composition according to the present invention are likely to be visible light actuatable rather than long wavelength UV actuatable.

For this reason, adhesive wound dressings intended for domestic use will preferably include light occlusive layers to prevent premature switching of the switchable adhesive composition, since premature switching would render the adhesive wound dressing ineffective because it would not stick to the skin sufficiently well and would peel from the skin too easily. The first light occlusive layer can form part of the release paper that is placed on the adhesive side of the dressing that is intended to be stuck to the skin. This first light occlusive layer is removed just before the adhesive wound dressing is applied over a wound. A second light occlusive layer is positioned on the opposite side of the adhesive wound dressing and remains in place until such time as the user wants to remove the adhesive wound dressing. At this point, the second light occlusive layer is removed, exposing the underlying switchable adhesive composition. Upon exposure to visible light, the switchable adhesive composition is transformed from its tacky state to a non-tacky or low-tack state. As a result, the peel force required to remove the adhesive wound dressing is reduced considerably and the dressing can be removed from the skin very easily.

On the other hand, adhesive wound dressings applied by trained medical practitioners may use a switchable adhesive composition that is actuatable by irradiation with long wavelength UV because trained medical practitioners are more likely to have access to a suitable UV lamp. In this case, light occlusive layers are not necessary. Instead, the upper surface of the adhesive wound dressing (i.e., the non-skin-contacting surface) only needs to be transparent or semitransparent to long wavelength UV light. When it is desired to remove the adhesive wound dressing, the trained medical practitioner shines a suitable UV light source over the adhesive wound dressing. As a result, the switchable adhesive composition is transformed from its tacky state to a non-tacky or low-tack state. As a result, the peel force required to remove the adhesive wound dressing is reduced considerably and the dressing can be removed from the skin very easily.

Surgical Incision Drapes

Although the occurrence of surgical site infections can vary from surgeon to surgeon, from hospital to hospital, from patient to patient, and also in accordance with the surgical procedure that is being conducted, it is believed that most surgical site infections are caused by the patient's own normal skin flora which enter the body through the surgical incision. The reason for this is that the patient's skin flora can move from the skin surface to the incision very easily. Also, innocuous bacterial flora on the patient's skin may also be host to pathogenic organisms.

Various surgical site infection countermeasures have been developed over the years to reduce the risk of such infections to patients. Obvious steps such as hygiene management of the operating room personnel and the operating room itself can lower the incidence of exogenous pathogens. Also, the scheduling of elective surgery so that it is conducted when patients have generally good health and hence concomitant healthy immune systems are also thought to be effective. Of course, not all surgery can be timetabled in this way and it is inevitable that many patients will have to undergo surgery when their health is far from perfect.

The application of bactericidal or antimicrobial agents to the patient's skin at the intended site of surgery has, in the past, been effective to kill bacteria. Various pre-operative skin preparation products, washes, surgical scrub tissues, wound cleaners, lotions and ointments have been used for many years for this purpose. However, with the emergence of bacteria that are resistant to antibiotic treatment, the effectiveness of such infection countermeasures is becoming lessened.

Longer lasting antimicrobial effects may be obtained by combining the antimicrobial agent applied pre-operatively with a surgical incision drape, for example in the form of a clear polymeric film with an adhesive backing on one side covered with a release liner. The release liner is removed and the surgical incision drape is placed over the intended site of incision, adhesive side down, and pressed into place on the patient's skin.

Unfortunately, known surgical drapes of this type can be lifted during surgery, which results in entry of bacteria into the surgical site. The lifting of the surgical drape is usually caused by failure of the adhesive to remain in contact with the patient's skin. Increasing the adhesive strength is not necessarily the ideal solution to this problem because more force is then required to remove the drape from the skin, which may result in damage of the skin near the surgical site.

As well as being switchable from a tacky state to a non-tacky or low-tack state upon exposure to long wavelength UV radiation or visible light, the switchable adhesive compositions of the present invention also undergo a change in their viscoelastic properties during switching. In the unswitched state, the adhesive compositions are viscoelastic and are able to flow into irregularities and pores, such as pores in a patient's skin surface. Good "wetting" occurs. In the switched state, the adhesive compositions are elastic and will move with a patient's skin. If required, they can be made to stay in position on a patient's skin, rather than being removed as described above in the discussion of adhesive wound dressings, by making the surface of the carrier film that supports the adhesive composition very slippery. In these circumstances, the switched adhesive remains preferentially attached to skin and is not removed when the supporting carrier film is removed.

This ability of switchable adhesive compositions according to the present to be made to adhere preferentially to the skin rather than to any carrier layer on which they are supported makes them suitable as surgical drapes.

Rather than using an adhesive as the medium to adhere a clear plastic film to the intended incision site, surgical incision drapes in accordance with the present invention use the adhesive itself as the material of the incision drape.

For use as a surgical incision drape, a medical skin covering is supplied as a layer of a switchable adhesive composition in accordance with the present invention sandwiched between two release liners. The release liners may include a light occlusive layer to prevent premature curing of the curable molecules of the switchable adhesive composition by exposure to incident light. Alternatively, the surgical incision drape may be packaged in a light occlusive covering that is removed before the surgical incision drape is deployed. The first release liner is removed just before the surgical incision drape is applied to the intended site of incision. Then the surgical incision drape is pressed on to the surface of the patient's skin at the intended site of incision, with the second release liner being uppermost and the adhesive composition layer being next to the patient's skin. The adhesive composition of the surgical incision drape is initially viscoelastic and is able to flow into irregularities and pores in the patient's skin surface and good "wetting" occurs. If necessary, any light occlusive layer on the second release liner is removed. Then the adhesive composition layer of the surgical incision drape is exposed to UV light or visible light through the second release liner to effect curing of the curable molecules in the adhesive composition. The resultant cured adhesive composition layer is elastic, and therefore moves with the patient's skin, but it is no longer visco-elastic and cannot easily be removed from the skin. Removal of the second release liner after curing leaves the elastic adhesive composition in place as a thin layer on the patient's skin. Preferably, the thin adhesive composition layer left in place on the patient's skin is transparent so that it is possible for the surgeon to see any markings that may have been made on the patient's skin before commencement of the surgical procedure. There is no wrinkling of the adhesive composition layer to obscure the surgeon's view of the incision site and the surgeon is able to make the incision through the cured elastic adhesive composition layer. Migration of the patient's normal skin flora, if not removed by pre-operative swabbing, is inhibited by the adhesive overlayer.

Towards the end of the surgical procedure, when the incision is to be closed, the cut edges of the skin are brought together and sutured, stapled or taped in the usual way through the switched adhesive composition layer that constitutes the surgical incision drape. Because of its adherence to the skin, the switched adhesive composition layer is difficult to peel away from the edges of the incision so is preferably left in position. Following closure of the incision, an area around the site of the incision may be cleared of the adhesive composition layer, although this is not necessary, to leave the incision site ready to receive a dressing.

Bacterial Barrier

After surgery, as described above, the switchable adhesive composition according to the present invention may find further use as a bacterial barrier applied over the closed incision site.

As discussed above, if a surgical drape in accordance with a first aspect of the invention has been used during the surgical procedure, an area around the site of the incision may be cleared of the adhesive composition layer that constituted the incision drape, for example by peeling away the adhesive composition layer. The cleared site is then disinfected by wiping it with an antibacterial wipe, in the usual way, so that it is then ready to receive a bacterial barrier.

Alternatively, the bacterial barrier may be applied directly over the surgical incision drape without any prior clearing of the surgical incision drape from the area around the site of the incision. Preferably, before applying the bacterial barrier, the intended site of its application is disinfected, for example by wiping with an antibacterial wipe.

In other situations, a bacterial barrier may be applied to a wound sustained through injury. The wound site is first cleaned and disinfected before applying the bacterial barrier.

Such bacterial barrier comprises a layer of a switchable adhesive composition in accordance with the present invention sandwiched between two release liners. The adhesive composition layer is initially viscoelastic prior to curing, but is transformable to an elastic state by curing of the curable molecules by exposure to UV or visible light. The release liners may include a light occlusive layer to prevent premature curing of the curable molecules of the adhesive composition by exposure to incident light. Alternatively, the bacterial barrier may be packaged in a light occlusive covering that is removed before the bacterial barrier is deployed. To apply the bacterial barrier to the closed incision site or over the wound, the first release liner is removed and the bacterial barrier is applied over the site of the closed incision or the wound, adhesive side down, pressing gently on the remaining release liner. The viscoelastic adhesive composition flows into the surface irregularities and pores of the patient's skin, including the edges of the incision or the edges of the wound. If necessary, any light occlusive layer on the second release liner is removed. The curable molecules in the adhesive composition layer are then caused to cure by exposure to UV light or visible light through the second release liner, causing the adhesive composition layer to change from its viscoelastic state to an elastic state. In the elastic state, the adhesive composition layer is no longer flowable, but is elastic so that it remains conformable with the patient's skin over the closed incision site, as the patient moves about.

The second release liner is removed after the curing step and the patient "wears" the bacterial barrier in the form of a cured elastic adhesive composition layer. If required, a dressing may be placed over the bacterial barrier, for example to relieve direct pressure on the closed site of the incision or wound.

Any bacteria remaining on the patient's skin prior to applying the bacterial barrier become immobilised in the cured adhesive composition layer and cannot migrate into the closed incision site or wound. The cured adhesive composition layer is breathable and allows moisture to escape from the pores of the patient's skin. Good wound healing is promoted by this breathability and by the exclusion of bacteria. The bacterial barrier eventually sloughs away with the shedding of skin cells from the surface of the patient's skin as wound healing progresses.

When the wound has healed sufficiently to permit removal of any sutures or staples, these can be removed without requiring the bacterial barrier to be removed beforehand. Rather, the sutures or staples can be removed through the bacterial barrier that remains if it has not already fallen away with the patient's dead skin cells.

Skin Closure

In a further aspect, the present invention may find use in skin closure applications.

In recent times, cyanoacrylate adhesives have found widespread use as an alternative to the traditional methods of suturing and/or stapling and/or taping for closing wounds. Such cyanoacrylate adhesives are fast and relatively simple to use; they are also comfortable for the patient to wear. They form an effective bacterial barrier and, from the physician's point of view, there is no risk of needle sticks. Finally, there is no need for a second visit to the physician for removal of the cyanoacrylate adhesive because it sloughs away with the patient's dead skin cells as wound healing progresses.

However, there are a number of disadvantages to using such cyanoacrylate adhesives in a skin closure application. Firstly, they give rise to toxic vapours when applied and during the cure; they undergo a pronounced exothermic reaction when curing, resulting in a burning sensation on the patient's skin. There is also a risk of scarring from adhesive flowing into the wound and, for wounds close to the eye, a risk of the adhesive entering into the patient's eye and sticking the eyelids together and/or sticking the eyelids to the eyeball. The curing speeds of cyanoacrylate adhesives depend on the formulation, but as curing is triggered by moisture, they can cure very rapidly on the patient's skin as a result of the moisture present at the skin surface. Sometimes, curing is too rapid and occurs before the edges of the wound have been properly brought together. Although simple to use in theory, mishandling of the cyanoacrylate adhesive as a skin closure medium can result in the adhesion of foreign objects to the wound, including the physician's fingertips or gloves.

The skin closure product using a switchable adhesive composition according to the present invention does not suffer from these drawbacks.

As with the surgical incision drape and bacterial barrier products described above, the skin closure product the present invention is most conveniently supplied as a layer of a switchable adhesive composition in accordance with the present invention sandwiched between two release liners. The release liners may include a light occlusive layer to prevent premature curing of the curable molecules of the adhesive composition by exposure to incident light. Alternatively, the skin closure product may be packaged in a light occlusive covering that is removed before the skin closure product is deployed. The curable molecules in the viscoelastic adhesive composition layer are curable to an elastic state by exposure to UV light or visible light.

In applying the skin closure product to a patient, the first release liner is removed and the skin closure product is placed on the patient's skin, adhesive side down, at one end of the wound to be closed. The physician uses the thumb and fingers of one hand to close together the edges of the skin of the wound and uses his other hand to press down the skin closure product progressively along and over the wound as the wound edges are progressively brought together.

When the skin closure product has been applied along the length of the wound, any light occlusive layer on the second release liner is removed. The curable molecules in the adhesive composition layer are then caused to cure by exposure to UV light or visible light through the second release liner. After curing, the second release liner is removed and a layer of the adhesive composition remains in place on the patient's skin. In its cured state, the adhesive composition layer is elastic and moves with the patient's skin, but has sufficient tensile strength to keep the edges of the wound together.

Curing of the curable molecules in the adhesive composition by radiation through the second release liner means that there is no risk of foreign objects becoming adhered to the wound and no risk of the physician's fingertips or gloves becoming adhered to the wound.

The cured adhesive composition layer is breathable and allows moisture to escape from the pores of the patient's skin. Moreover, the cured adhesive composition layer has good water resistance and does not require special care by the patient when bathing or showering.

The adhesive composition layer is gradually sloughed away with the patient's dead skin cells as wound healing progresses.

In yet another embodiment, a curable skin closure composition comprising low cytotoxicity oligomeric curable molecules as described herein may be dispensed from a tube, in similar fashion to the known cyanoacrylate adhesive skin closure products. The skin closure composition thus dispensed is spread on the patient's skin as the edges of the wound are held together by the physician or nurse. Then, the curable molecules in the applied skin closure composition are cured by irradiation using UV light or visible light, for example shone from a lamp aimed at the wound. After curing, the upper surface (i.e., the non-skin contact surface) of the applied skin closure layer may be slightly tacky as a result of exposure to oxygen in the ambient air which inhibits the free radical polymerization of the curable molecules in the composition at the exposed surface.

This can be rectified in a number of ways, for example by applying a bacterial barrier of the type described above, or by applying a second layer of the skin closure composition dispensed from the tube and immediately spreading it on the patient's skin by the act of applying a siliconised transparent release liner over the dispensed adhesive. Then, the curable molecules in the second layer of the skin closure composition are cured by irradiation through the release liner using UV light or visible light. After curing of the second layer of the skin closure composition, the release liner is removed as described above, to leave twin layers of the cured elastic skin closure composition in place over the wound site, the upper layer having no residual tackiness.

Alternatively, inhibition of the free radical polymerization of the curable molecules at the exposed surface can be reduced by including in the skin closure composition a component containing aliphatic thiol groups. Besides having oxygen-scavenging properties, the aliphatic thiols can also take part in the radical polymerization of the curable molecules via thiol-ene reactions. For a more effective contribution to the curing reaction, a component with two or more thiol groups could be used, such as trimethylolpropanetris (3-mercaptopropionate) or pentaerythritol tetrakis(2-mercaptoacetate). Amine synergists such as triethanol amine or ethyl-4-dimethylaminobenzoate could also be used to reduce oxygen inhibition of the radical polymerization at the exposed surface when this is not protected by a film.

The invention will be further described by way of example only and without limitation by reference to the drawings in which.

Figure 24:
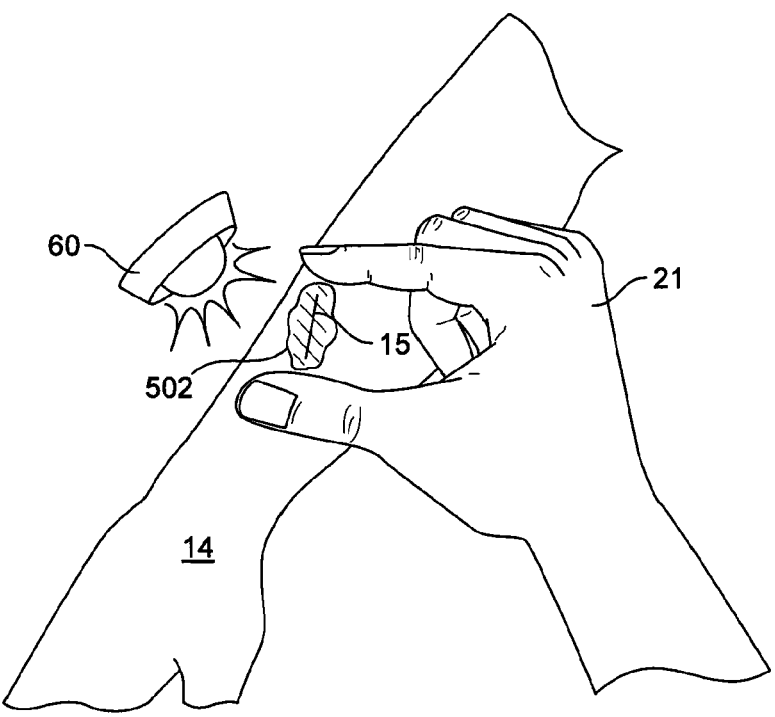
Figure 25:
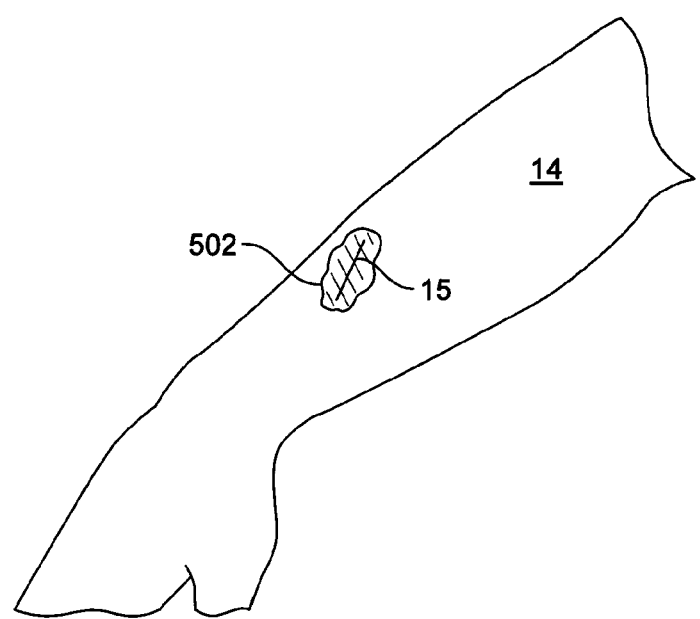

FIG. 24 is a perspective view of a film of the skin closure composition in accordance with the fifth embodiment of the invention in position on a patient's skin and in the act of being irradiated to effect curing of the composition; and FIG. 25 is a perspective view showing the cured skin closure film in accordance with the fifth embodiment of the invention in position over a closed wound on a patient's skin.

FIRST EMBODIMENT

A first embodiment of the present invention in the form of an adhesive medical dressing will now be described with reference to FIGS. 1 to 5.

Figure 1:
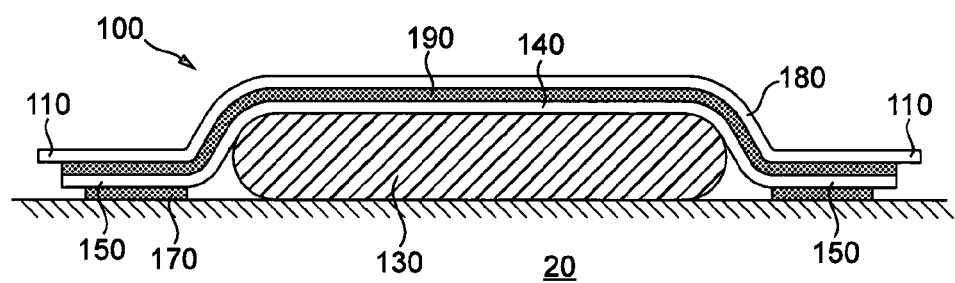
FIG. 1 is a cross-sectional view through an adhesive dressing in accordance with a first embodiment of the invention.

FIG. 1 is a cross-sectional view through an adhesive medical dressing 100 attached to a patient's skin 20. The adhesive medical dressing 100 is a multi-layer product having the following structure. The dressing 100 comprises a wound facing absorbent layer 130 disposed beneath a protective backing layer 140. At opposed edges 150, the backing layer 140 is provided with a switchable adhesive composition 170 which includes the low cytotoxicity oligomeric curable molecules described above that can be cross-linked under the influence of UV and/or visible light.

The backing layer 140 is provided with a light occlusive cover layer 180 which is releasably secured to the backing layer 140 by a weak adhesive 190. In an alternative arrangement, not shown here, the light occlusive cover layer 180 may be laminated to the backing layer 140. For ease of removal, the light occlusive cover layer 180 overlaps the backing layer 140 at its edges 110.

When it is desired to remove the dressing from the skin of the patient, the light occlusive cover layer 180 can be gripped at its edges 110 and peeled from the backing layer 140 to expose the underlying adhesive composition layer 170. Irradiation of the adhesive composition layer 170 with UV or visible light acts so as to generate free radicals that cause the curable molecules in the adhesive composition mixture to undergo a curing reaction which, after a certain time (depending upon the adhesive composition mixture used), causes the adhesive composition 170 to lose its tackiness to such an extent that the dressing 100 can be removed without causing trauma to the patient.

In order that the removal of the light occlusive cover layer 180 does not itself cause trauma to the patient, the peel strength of the adhesive 190 adhering the light occlusive cover layer 180 to the backing layer 140 should be less than the peel strength of the adhesive 170 adhering the dressing 100 to the patient's skin 20.

Since the adhesive composition 170 loses tackiness on exposure to visible and/or UV light, it is desirable that the adhesive 70 is not exposed to such light for a substantial period when the dressing 100 is applied to a patient. Thus, the adhesive composition 170 may be initially provided on the surface with release paper (see FIG. 3) which is preferably opaque to UV and visible light and which can be readily removed from the adhesive so that the dressing is ready for use when required.

Figure 2:
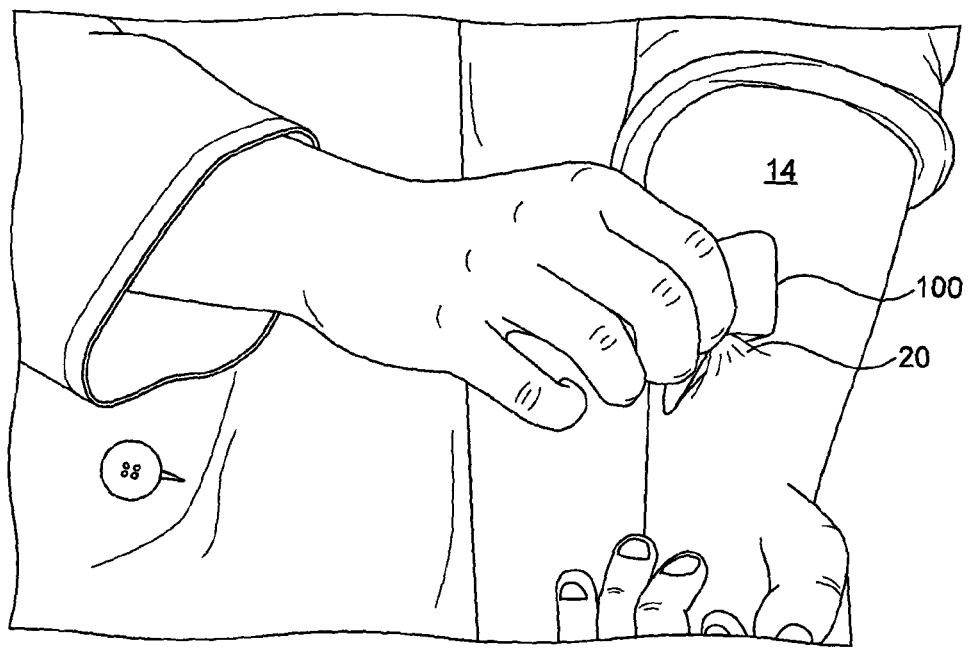
FIG. 2 is a perspective view showing the attempted removal from a patient's forearm of an adhesive dressing in accordance with the first embodiment of the invention.

FIG. 2 is a perspective view showing a patient attempting to remove an adhesive dressing 100 in accordance with the first embodiment of the invention from his forearm 14. Before switching, the adhesive composition 170 is very tacky and firmly sticks the adhesive dressing 100 to the patient's skin 20. Hence, when the patient attempts to lift one of the corners of the dressing 100, his skin 20 becomes stretched and the dressing 100 remains attached to the skin.

Figure 3:
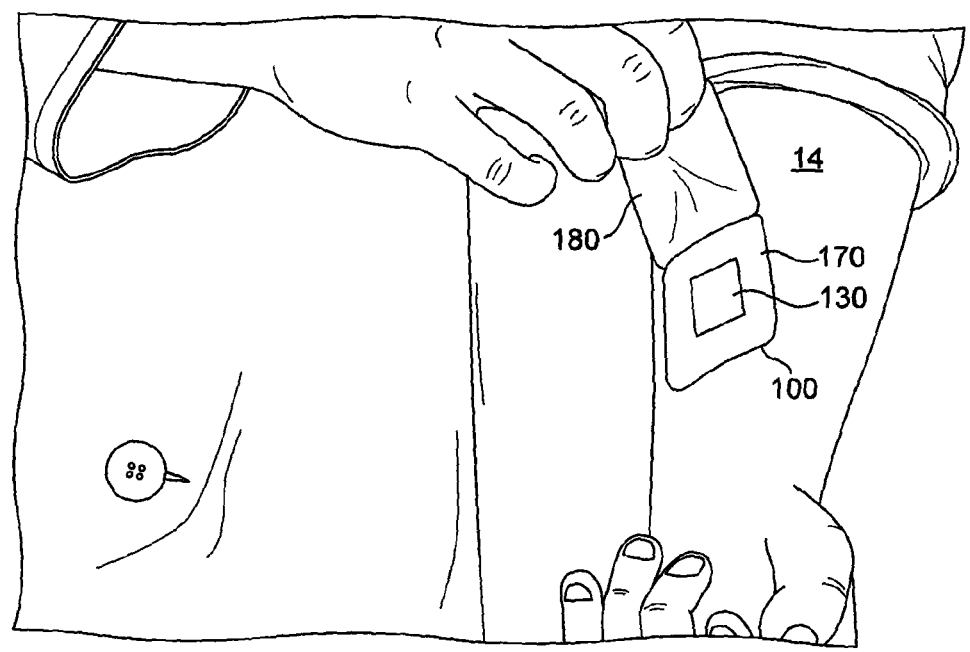
FIG. 3 is a perspective view showing removal of a light occlusive layer from the adhesive dressing in accordance with the first embodiment of the invention.

FIG. 3 is a perspective view showing the patient removing the light occlusive cover layer 180 from the adhesive dressing 100 to expose the underlying adhesive composition 170. In this view, the wound pad 130 can also be seen.

Figure 4:
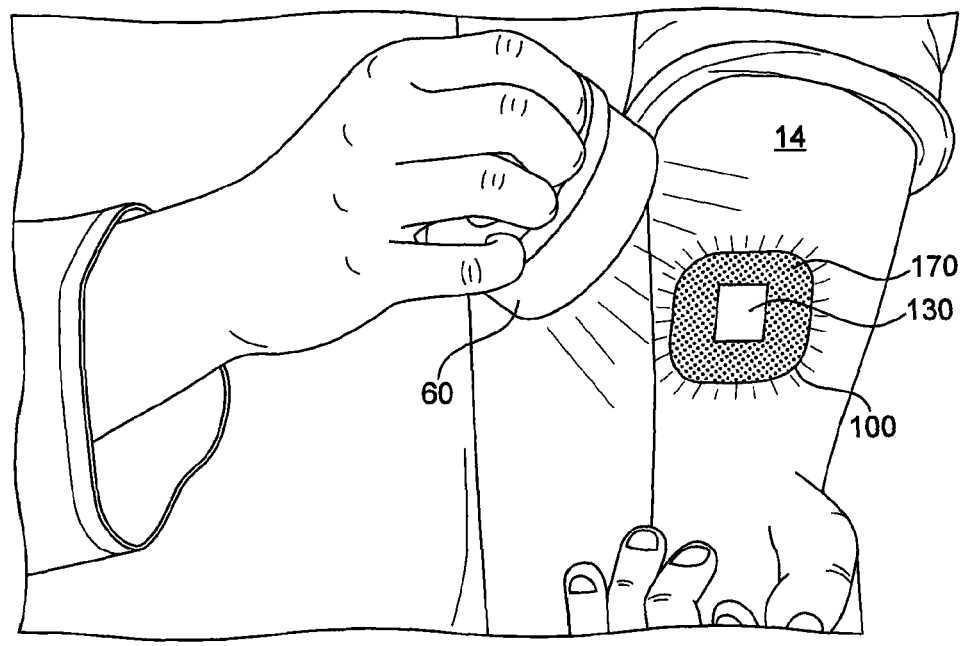
FIG. 4 is a perspective view showing the adhesive dressing in accordance with the first embodiment of the invention undergoing irradiation to effect switching of the adhesive.

FIG. 4 is a perspective view showing the adhesive dressing undergoing irradiation, in this example from a lamp 60, to effect cure of the curable molecules in the adhesive composition 170. The light from the lamp 60 (UV light or visible light, preferably long wavelength UV light) causes the photoinitiator in the adhesive composition 170 to generate free radicals that initiate curing of the curable molecules in the adhesive composition. Curing transforms (switches) the adhesive composition 170 from its tacky state to a non-tacky or low-tack state.

Figure 5:
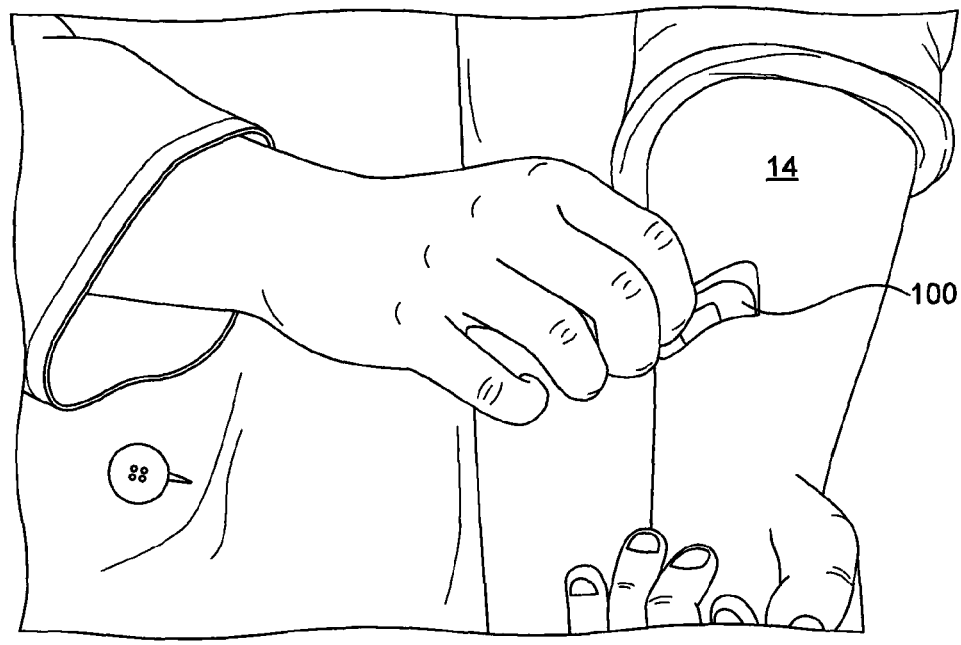
FIG. 5 is a perspective view showing how the adhesive dressing in accordance with the first embodiment of the invention may be easily removed after switching of the adhesive.

FIG. 5 is a perspective view showing how, after switching of the adhesive composition, the patient is easily able to remove adhesive dressing 100 from his forearm 14.

SECOND EMBODIMENT

A second embodiment of the present invention in the form of a surgical incision drape will now be described with reference to FIGS. 6 to 11.

Figure 6:
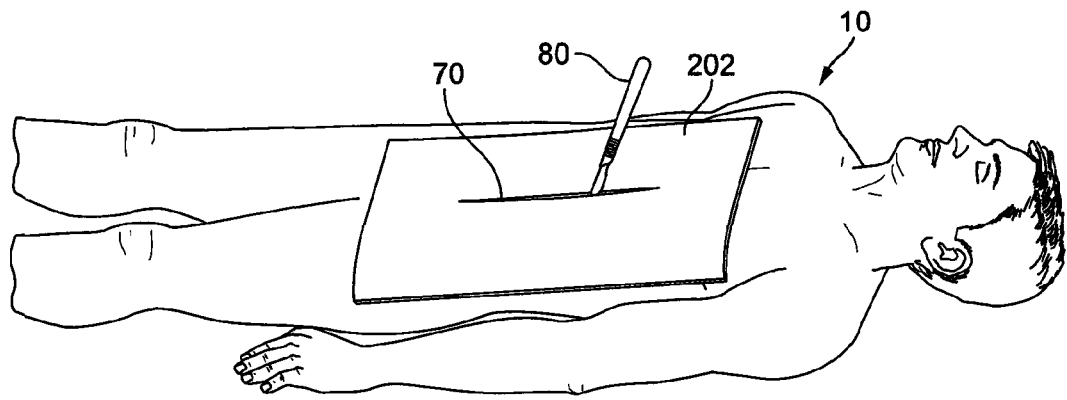
FIG. 6 is a perspective view showing an incision being made through a surgical incision drape according to a second embodiment of the present invention.

FIG. 6 is a perspective view showing a scalpel 80 making an incision 70 in the torso of a patient 10 through the adhesive layer 202 of a surgical incision drape in accordance with a second embodiment of the invention. The physician's hand holding the scalpel has been omitted from FIG. 6 for clarity.

Figure 7:
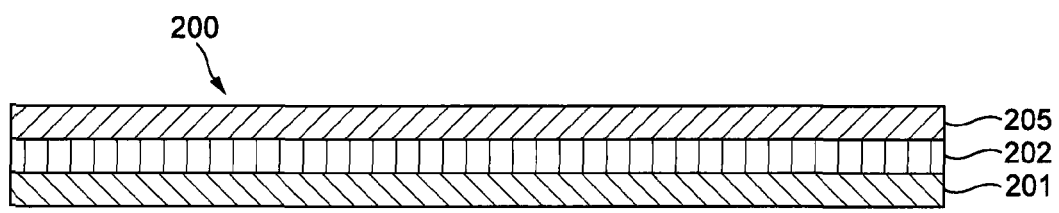
FIG. 7 is a cross-sectional view through the surgical incision drape in accordance with the second embodiment of the invention.

As shown in cross-sectional view in FIG. 7, the surgical incision drape 200 is a multiple layer article. The adhesive layer 202 is sandwiched between a first release liner 201 and a second release liner 205.

The first release liner 201 is a layer of siliconised plastic film, siliconised on the surface that faces the adhesive layer 202. In addition, the first release liner 201 is an occlusive material that prevents UV light and/or visible light passing through it and reaching the underlying adhesive layer 202.

The second release liner 205 is siliconised on the surface that faces the adhesive layer 202. Siliconised second release liner 205 is transparent to UV radiation and/or visible light. The siliconised second release liner 205 remains in place whilst the curable molecules in the adhesive layer 202 undergo curing by irradiation with UV light or by irradiation with visible light.

The occlusive first release liner 201 prevents inadvertent curing of the curable molecules in the adhesive layer 202 before the intended time by preventing the adhesive layer 202 from being exposed to UV light or visible light.

Figure 8:
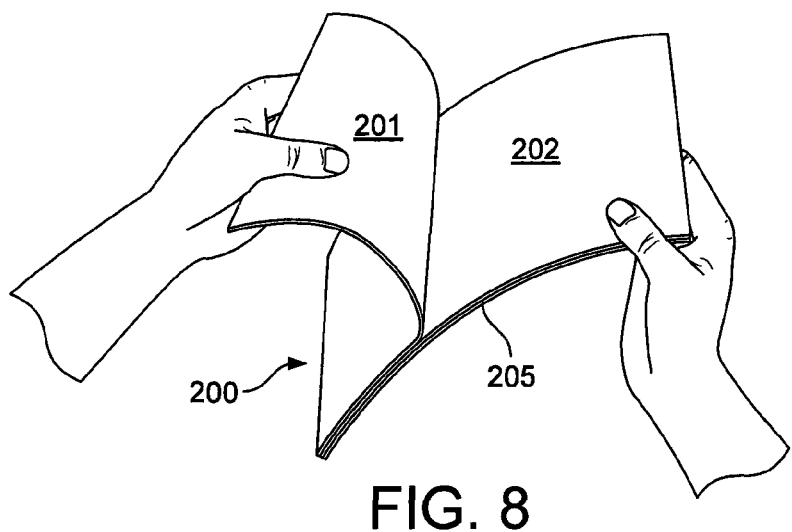
FIG. 8 is a perspective view showing the act of removal of one of the release liners of the surgical incision drape according to the second embodiment of the present invention.

FIG. 8 is a perspective view of the surgical incision drape 200 showing the removal of the first release liner 201 to expose the underlying adhesive layer 202. The second release liner 205 is still in place on the other side of the adhesive layer 202. After removal of the first release liner 201, the surgical incision drape 200 is quickly positioned over the site of the intended incision to minimise exposure of the adhesive layer 202 to any radiation that might bring about curing of the adhesive, and also to minimise exposure of the uncured adhesive to atmospheric oxygen. Positioning of the surgical drape is discussed in the next paragraph.

Figure 9:
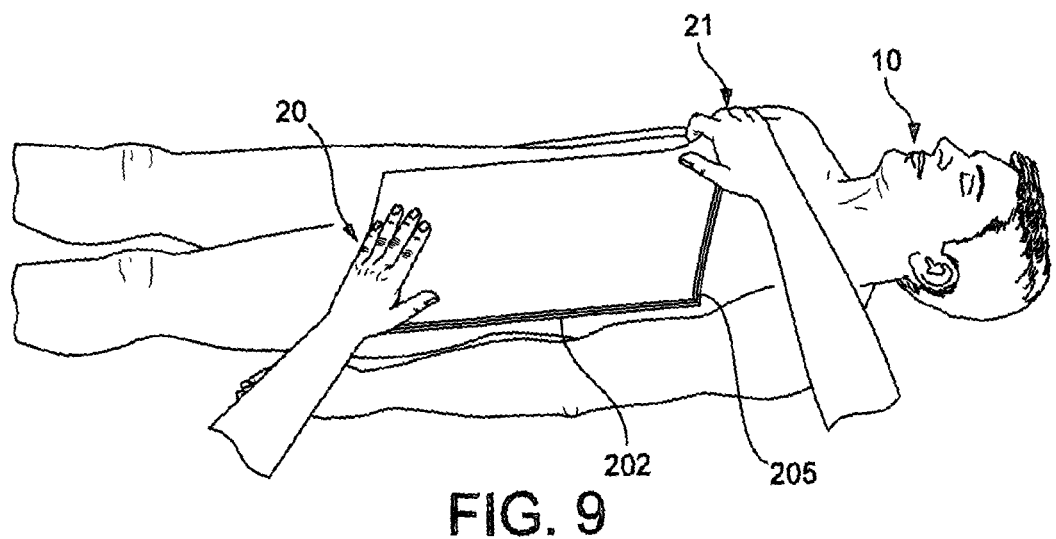
FIG. 9 is a perspective view of the surgical incision drape according to the second embodiment of the present invention in the act of being applied to the torso of a patient prior to surgery.

FIG. 9 is a perspective view showing the remaining layers of the surgical incision drape being applied to the torso of a patient 10 by the hands 20, 21 of a physician or nurse. In this view, the second release liner 205 is uppermost and the adhesive layer 202 is the layer that is brought into contact with the skin of the patient. The siliconised release surface of the second release liner 205 is next to the adhesive layer 202. Because the curable molecules of the adhesive composition of the adhesive layer 202 are uncured at this stage, the adhesive layer 202 is still in its viscoelastic state. In this state, the adhesive is able to flow into surface irregularities and pores of the skin to ensure intimate contact between the surgical incision drape and the patient's skin.

Figure 10:
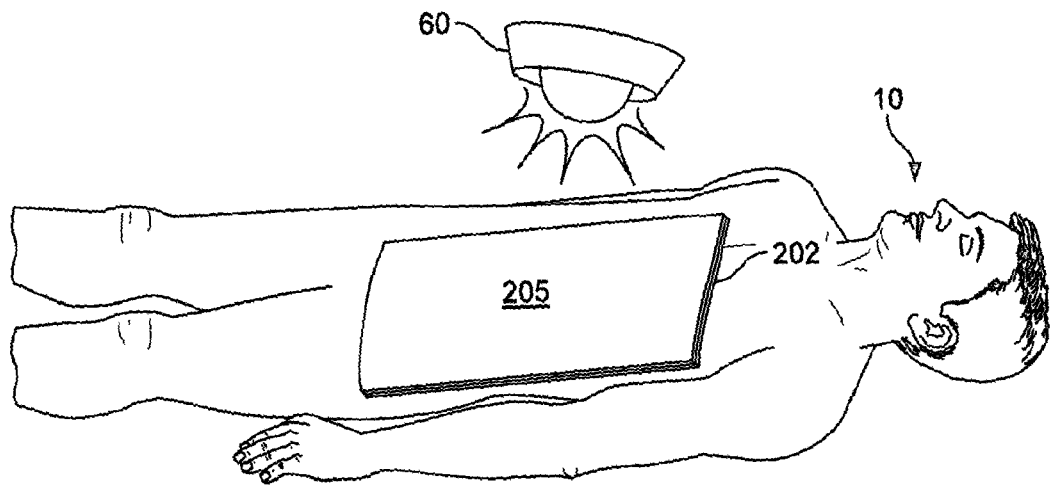
FIG. 10 is a perspective view of the surgical incision drape according to the second embodiment of the present invention in position on the torso of a patient and undergoing irradiation to effect cure of the adhesive.

FIG. 10 is a perspective view of the surgical incision drape in position on the torso of the patient 10 and undergoing irradiation, in this example from a lamp 60, to effect cure of the curable molecules in the adhesive composition of the adhesive layer 202. The light from the lamp 60 (UV light or visible light, preferably long wavelength UV light) passes through the transparent siliconised release liner 205 to the underlying adhesive layer 202 to initiate curing of the curable molecules in the adhesive composition. Curing transforms the adhesive composition layer from its viscoelastic state to an elastic state.

The transparent siliconised release liner 205 is retained in place over the adhesive layer 202 during the curing step to prevent oxygen in the ambient air from reacting with the adhesive composition as the curable molecules in the adhesive mixture undergo curing. Exposure to oxygen during curing causes the upper surface (i.e., the non skin contact surface) of the adhesive composition to remain slightly tacky after curing is complete. This slight tackiness is preferably avoided in a surgical incision drape because it may result in foreign objects (fluff, dust, etc.) becoming stuck to the surgical incision drape. Also, the slight tackiness may increase the possibility that parts of the surgical incision drape will be prematurely removed, for example by being abraded by contact with the physician's gloves. By retaining the siliconised release liner 205 in place over the adhesive layer 202 and curing the curable molecules in the adhesive layer 202 by irradiation through the siliconised release liner 205, the occurrence of surface tackiness in the cured adhesive composition layer is avoided.

Figure 11:
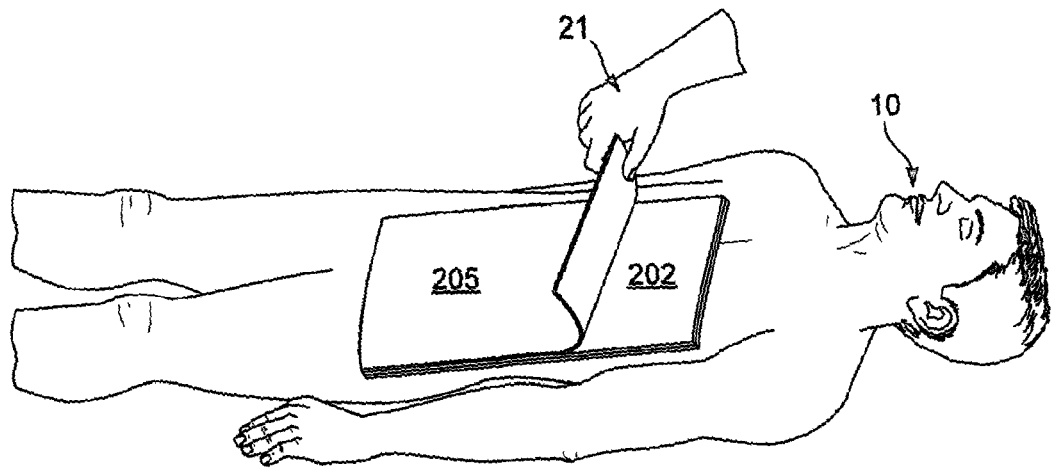
FIG. 11 is a perspective view showing the act of removal of the remaining layer of the second release liner of the surgical incision drape according to the second embodiment of the invention.

FIG. 11 is a perspective view showing the physician's hand 21 removing the siliconised release liner 205 from the adhesive layer 202 of the surgical incision drape after the curable molecules in the adhesive composition of the adhesive layer 202 have been cured. After removal of the siliconised release liner 205, only the cured adhesive composition layer 202 remains on the patient's skin.

Preferably, the cured adhesive composition layer is transparent so that the physician can see the site of the intended incision and any markings that may have been made on the patient's skin prior to commencement of the surgical procedure.

As mentioned above, in the cured state, the adhesive composition of the adhesive layer 202 is transformed from its initial viscoelastic state to an elastic state. In this state, the adhesive remains firmly stuck to the patient's skin but, by virtue of its elasticity, the adhesive layer is able to move with the patient's skin as the skin moves. Moreover, the cured adhesive layer is an effective barrier to bacteria. Any bacteria that remained on the surface of the patient's skin after the preliminary antibacterial swabbing step become immobilised in the cured adhesive layer and migration to the incision site is thereby inhibited.

Referring again to FIG. 6, the cured adhesive composition layer 202 of the surgical incision drape remains in position on the patient's skin and is incised, along with the patient's skin, when a physician (not depicted in FIG. 6) makes an incision 70 with a scalpel 80.

After surgery, the adhesive layer 202 at the edges of the incision may be peeled away so that the incision can be closed without interposition of any adhesive layer material between the mating skin edges. Closure of the incision may be performed in the usual way, for example by suturing or by means of surgical staples or surgical tapes. Alternatively, the adhesive composition layer 202 may be left in place during closure of the incision. If left in place, the adhesive composition layer 202 is gradually sloughed away with the shedding of skin cells from the surface of the patient's skin as healing takes place.

THIRD EMBODIMENT

A third embodiment of the present invention in the form of a bacterial barrier will now be described with reference to FIGS. 12 to 17.

Figure 12:
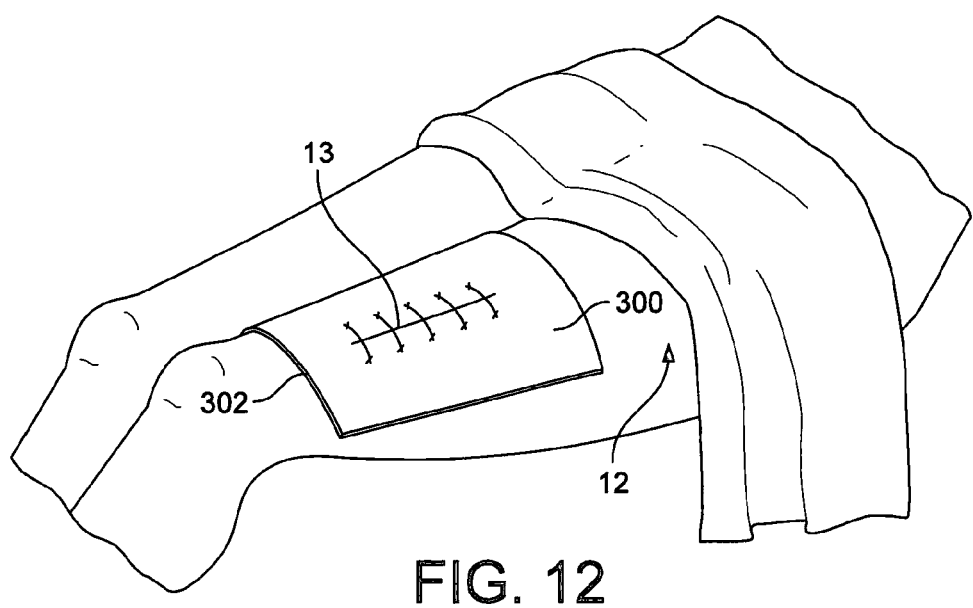
FIG. 12 is a perspective view of a bacterial barrier in accordance with a third embodiment of the present invention in place on a patient's thigh, overlying a sutured wound.

FIG. 12 is a perspective view showing a bacterial barrier 300 in accordance with the third embodiment of the invention in place on a patient's thigh 12, overlying a sutured wound 13. The bacterial barrier 300 in this view consists of a single layer 302 of cured adhesive composition, as will be explained in more detail below.

Figure 13:
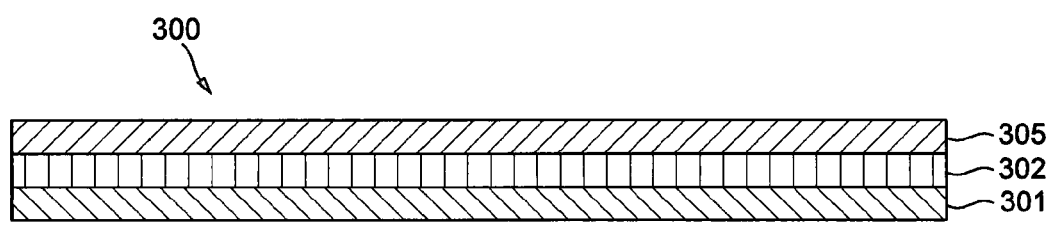
FIG. 13 is a cross-sectional view of the bacterial barrier in accordance with the third embodiment of the present invention.

As shown in cross-sectional view in FIG. 13, the bacterial barrier 300 is a multiple layer article. The adhesive layer 302 is sandwiched between a first release liner 301 and a second release liner 303.

The first release liner 301 is a layer of siliconised plastic film, siliconised on the surface that faces the adhesive layer 302. In addition, the first release liner 301 is an occlusive material that prevents UV light and/or visible light passing through it and reaching the underlying adhesive layer 302.

The second release liner 305 is also siliconised on the surface that faces the adhesive layer 302. Siliconised release liner 305 is transparent to UV radiation and visible light. The siliconised second release liner 305 remains in place whilst the curable molecules in the adhesive layer 302 undergo curing by irradiation with UV light or by irradiation with visible light.

The occlusive first release liner 301 prevents inadvertent curing of the curable molecules in the adhesive layer 302 before the intended time by preventing the adhesive layer 302 from being exposed to UV light or visible light.

Figure 14:
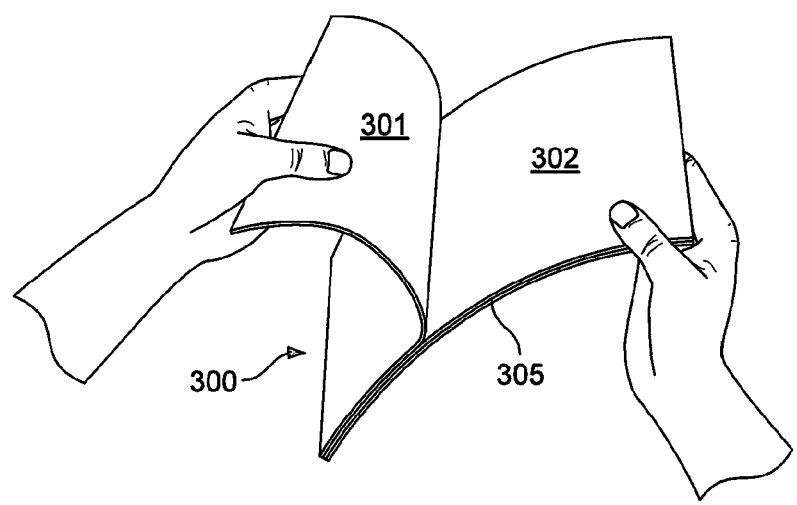
FIG. 14 is a perspective view showing the act of removal of the first release liner from the bacterial barrier according to the third embodiment of the invention.

FIG. 14 is a perspective view of the bacterial barrier 300 showing the removal of the first release liner 301 to expose the underlying adhesive layer 302. The second release liner 305, comprising its siliconised release surface, is still in place on the other side of the adhesive layer 302. After removal of the first release liner 301, the bacterial barrier 300 is quickly positioned over the site of the wound to be covered (see FIG. 12) so as to minimise exposure of the adhesive layer 302 to any radiation that might bring about curing of the curable molecules in the adhesive composition, and also to minimise exposure of the uncured adhesive composition layer to atmospheric oxygen. Positioning of the bacterial barrier is discussed in the next paragraph.

Figure 15:
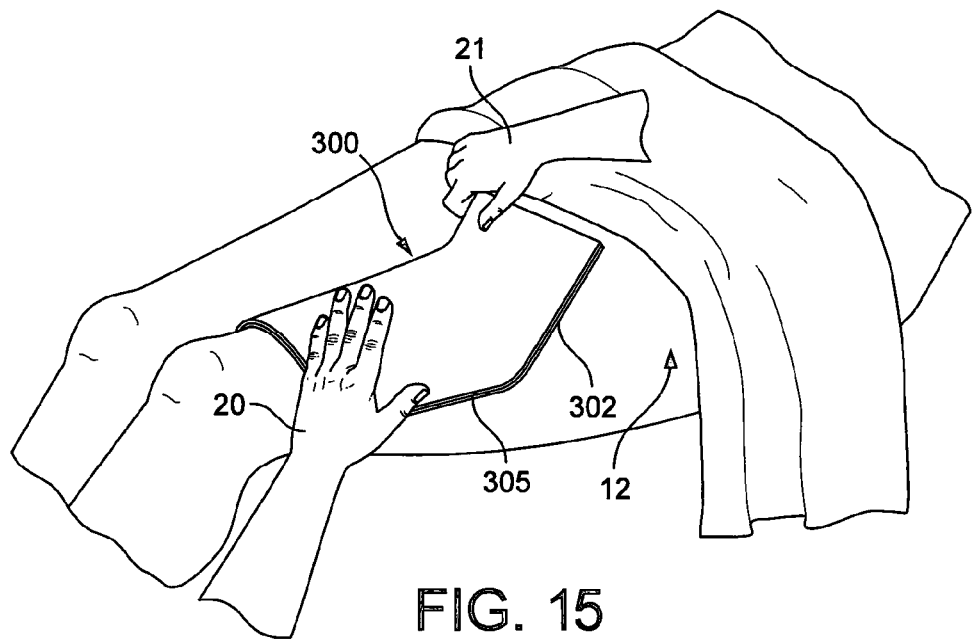
FIG. 15 is a perspective view of the bacterial barrier according to the third embodiment of the present invention being applied to the thigh of a patient to cover a sutured wound.

FIG. 15 is a perspective view showing the remaining layers of the bacterial barrier being applied to the thigh 12 of a patient by the hands 20, 21 of a nurse or physician. In this view, the second release liner 305 is uppermost and the adhesive layer 302 is the layer that is brought into contact with the skin of the patient. The siliconised release surface of the second release liner 305 is next to the adhesive layer 302. Because the curable molecules of the adhesive composition of the adhesive layer are uncured at this stage, the adhesive layer 302 is still in its viscoelastic state. In this state, the adhesive is able to flow into surface irregularities and pores of the skin to ensure intimate contact between the bacterial barrier in a surface and the patient's skin.

Figure 16:
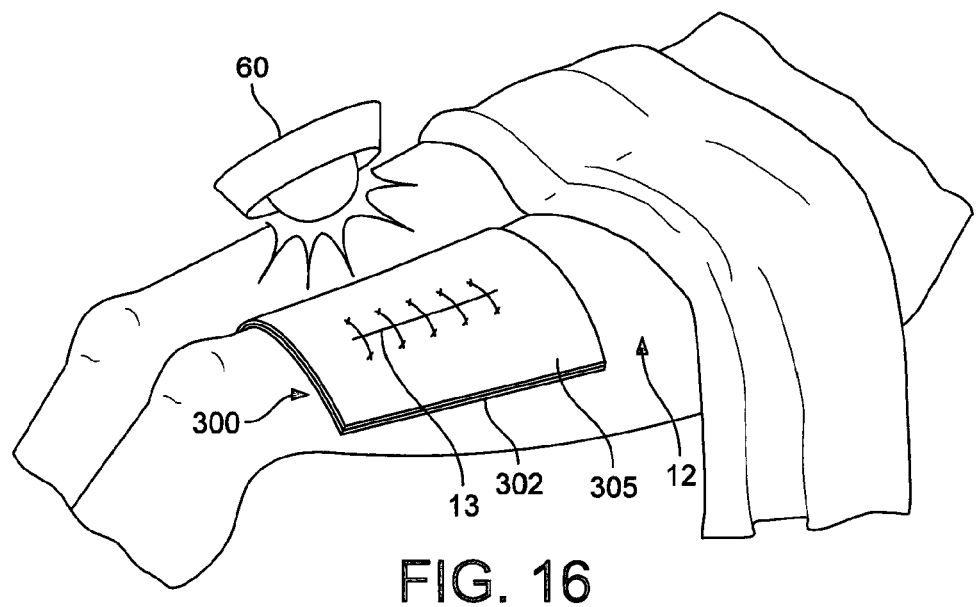
FIG. 16 is a perspective view of the bacterial barrier according to the third embodiment of the invention in position on a patient's thigh and in the act of being irradiated to cure the adhesive.

FIG. 16 is a perspective view of the bacterial barrier 300 in position on the thigh 12 of the patient and undergoing irradiation, in this example from a lamp 60, to effect cure of the curable molecules in the adhesive composition of the adhesive layer 302. The light from the lamp 60 (UV light or visible light, preferably long wavelength UV light) passes through the transparent siliconised second release liner 305 to the underlying adhesive layer 302 to initiate curing of the curable molecules in the adhesive composition. Curing transforms the adhesive composition layer from its viscoelastic state to an elastic state.

The transparent siliconised release liner 305 is retained in place over the adhesive layer 302 during the curing step to prevent oxygen in the ambient air from reacting with the adhesive composition as the curable molecules in the adhesive mixture undergo curing. Exposure to oxygen during curing causes the upper surface (i.e., the non skin contact surface) of the adhesive composition layer to remain slightly tacky after curing is complete. This slight tackiness is preferably avoided in a bacterial barrier because it may result in foreign objects (fluff, dust, etc.) becoming stuck to the bacterial barrier. Also, the slight tackiness may cause the bacterial barrier to be unintentionally removed, for example by being abraded by contact with the patient's clothes. By retaining the siliconised release liner 305 in place over the adhesive layer 302 and curing the curable molecules in the adhesive layer 302 by irradiation through the siliconised release liner 305, the occurrence of surface tackiness in the cured adhesive composition layer is avoided.

Figure 17:
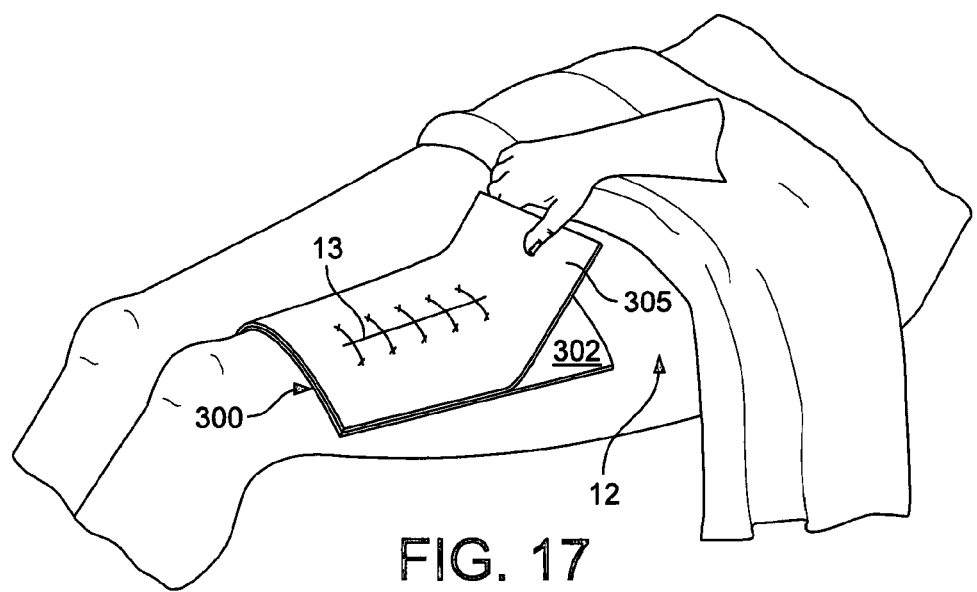
FIG. 17 is a perspective view showing the act of removal of the siliconised release layer of the bacterial barrier of the third embodiment of the invention, leaving just the cured adhesive layer in place on the patient's thigh.

FIG. 17 is a perspective view showing the physician's or nurse's hand 21 removing the siliconised second release liner 305 from the adhesive layer 302 of the bacterial barrier after the curable molecules in the adhesive composition of the adhesive layer 302 have been cured. After removal of the siliconised second release liner 305, only the cured adhesive composition layer 302 remains on the patient's thigh 12.

As mentioned above, in the cured state, the adhesive composition of the adhesive layer 302 is transformed from its initial viscoelastic state to an elastic state. In this state, the adhesive layer remains firmly stuck to the patient's skin but, by virtue of its elasticity, the adhesive layer is able to move with the patient's skin as the patient moves. The cured adhesive composition layer is an effective barrier to bacteria. Any bacteria that remained on the surface of the patient's skin after preliminary antibacterial swabbing become immobilised in the cured adhesive composition layer and migration to the site of the wound is thereby inhibited. The bacterial barrier is also a mechanical barrier against dirt and other foreign particles and substances.

Referring again to FIG. 12, the cured adhesive composition layer 302 of the bacterial barrier remains in position on the patient's skin over the wound 13. In practice, the wound 13 may be a wound that has arisen as a result of trauma to the patient or, as discussed above in relation to the second embodiment, the wound 13 may be the site of a surgeon's incision which has been sutured, stapled or taped closed after completion of the surgery.

The bacterial barrier is breathable and allows moisture to escape from the pores of the patient's skin. Moreover, the cured adhesive composition layer 302 has good water resistance and does not require special care by the patient when bathing or showering. Preferably, the cured adhesive composition layer 302 is transparent to allow inspection of the underlying skin surface without needing to remove the bacterial barrier.

The adhesive composition layer 302 is gradually sloughed away with the shedding of skin cells from the surface of the patient's skin as wound healing progresses.

FOURTH EMBODIMENT

A fourth embodiment of the present invention in the form of a skin closure film will now be described with reference to FIGS. 18 to 22.

Figure 18:
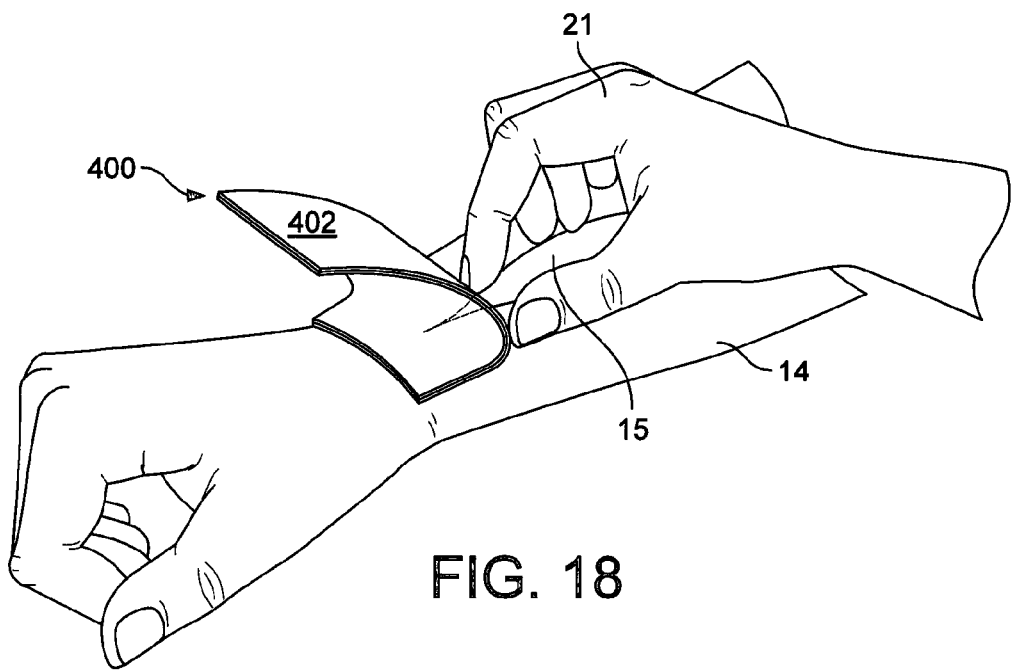
FIG. 18 is a perspective view showing a skin closure device according to a fourth embodiment of the invention in the act of being applied to a gaping wound on a patient's forearm as the skin edges are progressively brought together by a physician's thumb and fingers.

FIG. 18 is a perspective view showing a skin closure film 400 in accordance with the fourth embodiment of the invention being applied in place on a patient's forearm 14 for closing a gaping wound 15. The skin edges of the gaping wound 15 are shown being progressively urged together by the physician's or nurse's hand 21 as the skin closure film 400 is applied over the newly closed part of the wound 15. The second hand that the physician or nurse uses to apply the skin closure film 400 progressively to the newly closed part of the wound 15 is omitted from this view for reasons of clarity. The skin closure film 400 applied at this stage is a multiple layer product, as will be explained in more detail below.

Figure 19:
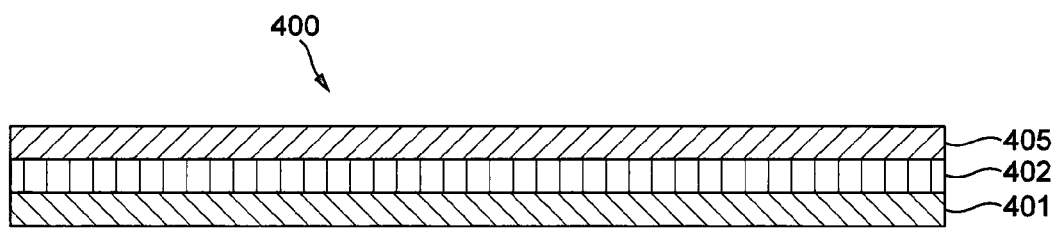
FIG. 19 is a cross-sectional view through the skin closure device in accordance with the fourth embodiment of the invention.

As shown in cross-sectional view in FIG. 19, the skin closure laminate 400 is a multiple layer article. The adhesive layer 400 is sandwiched between a first release liner 401 and a second release liner 405.

The first release liner 401 is a layer of siliconised plastic film, siliconised on the surface that faces the adhesive layer 402. In addition, the first release liner 401 is an occlusive material that prevents UV light and/or visible light passing through it and reaching the underlying adhesive layer 402.

The second release liner 405 is also siliconised on the surface that faces the adhesive layer 402. Siliconised release liner 405 is transparent to UV radiation and visible light.

The occlusive first release liner 401 prevents inadvertent curing of the curable molecules in the adhesive layer 402 before the intended time by preventing the adhesive layer 402 from being exposed to UV light or visible light.

Figure 20:
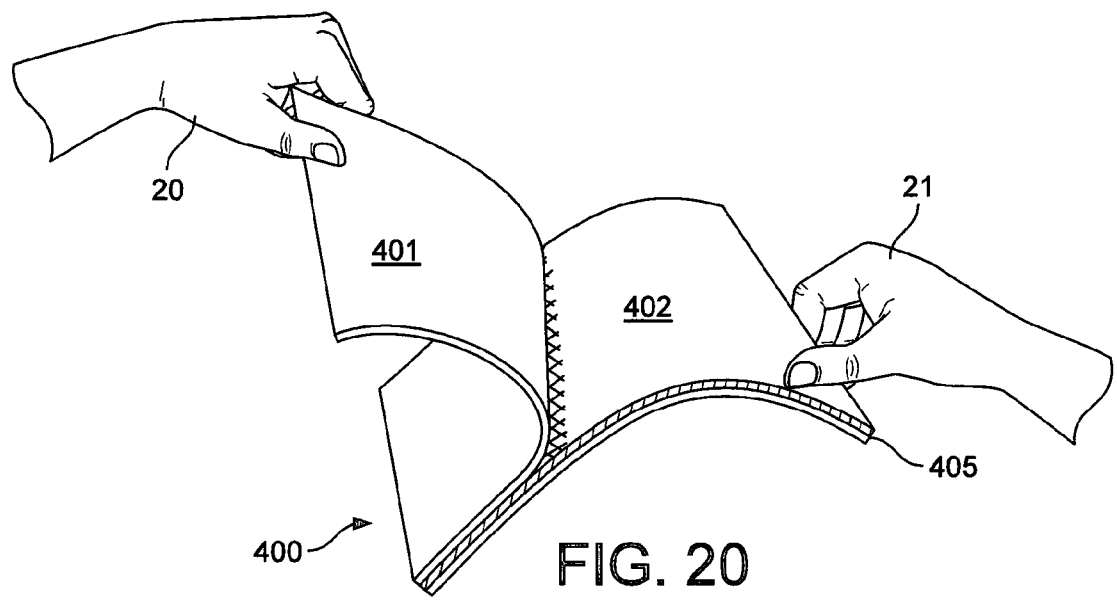
FIG. 20 is a perspective view showing the removal of the first release liner from the skin closure device in accordance with the fourth embodiment of the invention.

FIG. 20 is a perspective view of the skin closure laminate 400 showing the removal of the first release liner 401 to uncover the underlying adhesive layer 402. The second release liner 405 is still in place on the other side of the adhesive layer 402. After removal of the first release liner 401, the skin closure laminate 400 is preferably quickly positioned over the site of the wound to be closed (see FIG. 18) so as to minimise exposure of the adhesive layer 402 to any radiation that might bring about curing of the curable molecules in the adhesive, and also to minimise exposure of the uncured adhesive composition to atmospheric oxygen. Positioning of the skin closure laminate is discussed in the next paragraph.

Returning to FIG. 18, this is a perspective view showing the remaining layers of the skin closure laminate being applied to the forearm 14 of a patient by a nurse or physician. In this view, the second release liner 405 is uppermost and the adhesive layer 402 is the layer that is brought into contact with the skin of the patient. Because the curable molecules in the adhesive composition of the adhesive layer are uncured at this stage, the adhesive layer 402 is still in its viscoelastic state. In this state, the adhesive is able to flow into surface irregularities and pores of the skin to ensure intimate contact between the skin closure film and the patient's skin.

The adhesive layer 402 is beneath the siliconised second release liner 405 and in contact with the skin of the patient's forearm 14. The second siliconised release layer 405 is transparent to UV light and/or visible light, for reasons which will be explained below.

Figure 21:
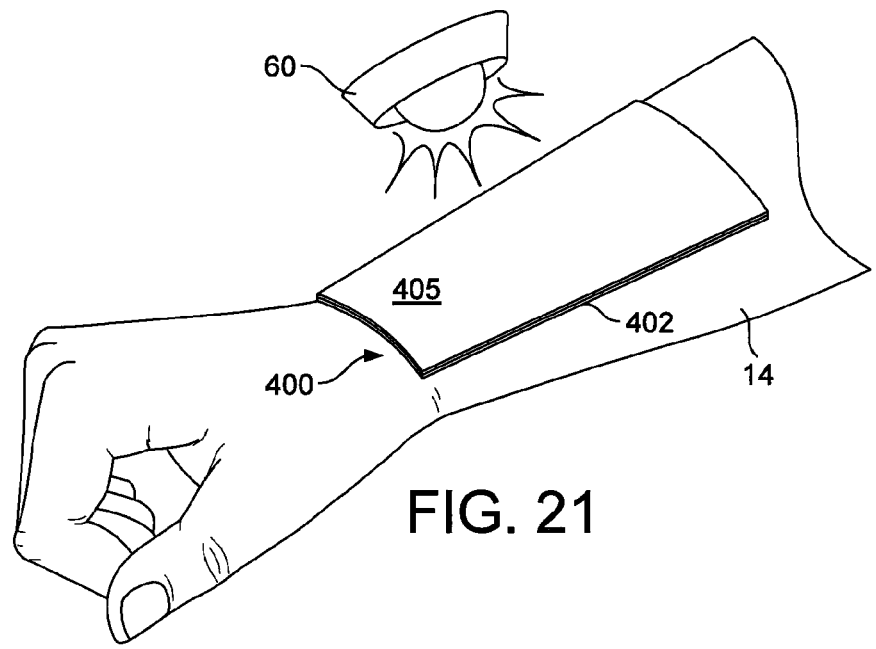
FIG. 21 is a perspective view of the skin closure device in accordance with the fourth embodiment of the invention in position on a patient's forearm and in the act of being irradiated to effect cure of the adhesive.

FIG. 21 is a perspective view of the skin closure laminate 400 in position on the forearm 14 of the patient and undergoing irradiation, in this example from a lamp 60, to effect cure of the curable molecules in the adhesive composition of the adhesive layer 402. The light from the lamp 60 (UV light or visible light—long wavelength UV is the preferred form of UV light) passes through the transparent siliconised release liner 405 to the underlying adhesive layer 402 to initiate curing of the curable molecules in the adhesive composition. Curing transforms the adhesive composition layer from its viscoelastic state to an elastic state.

The transparent siliconised release liner 405 is retained in place over the adhesive layer 402 during the curing step to prevent oxygen in the ambient air from reacting with the adhesive as the curable molecules in the adhesive mixture undergo curing. Exposure to oxygen during curing causes the upper surface (i.e., the non skin contact surface) of the adhesive composition layer 402 to remain slightly tacky after curing is complete. This slight tackiness is preferably avoided in a skin closure product because it may result in foreign objects (fluff, dust, etc.) becoming stuck to the skin closure film. Also, the slight tackiness may cause the skin closure film to be prematurely removed, for example by being abraded by contact with the patient's clothes. By retaining the siliconised release liner 405 in place over the adhesive layer 402 and curing the curable molecules in the adhesive layer 402 by irradiation through the siliconised release liner 405, the occurrence of surface tackiness in the cured adhesive composition layer is avoided.

Figure 22:
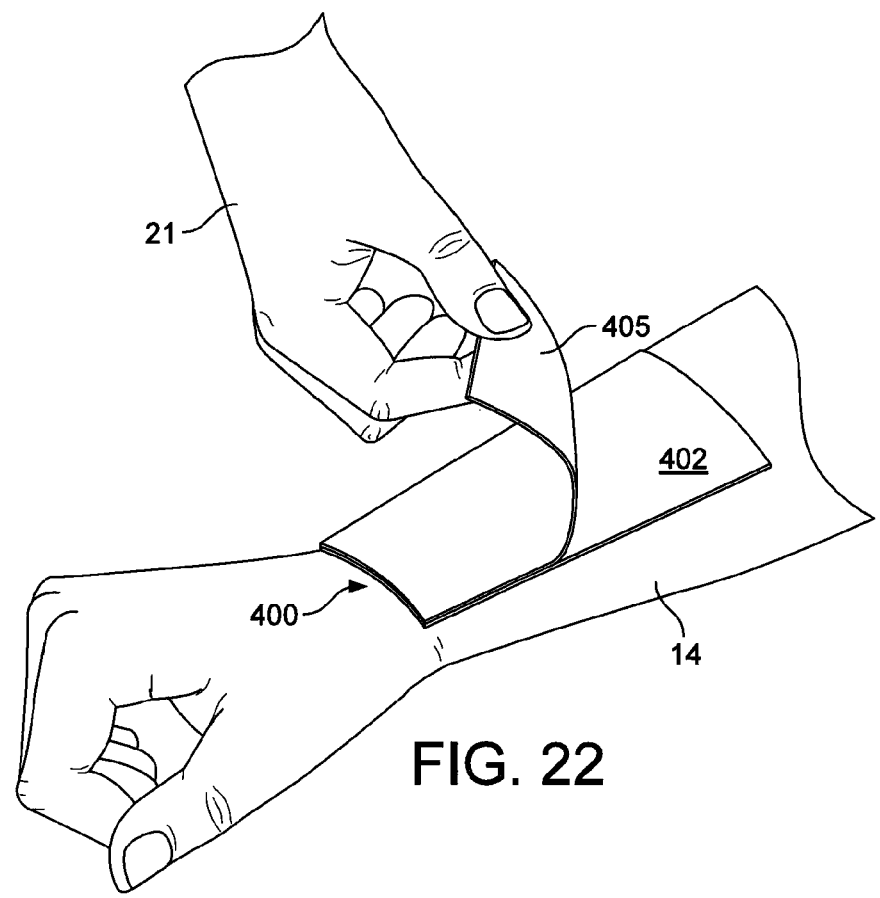
FIG. 22 is a perspective view showing the act of removal of the siliconised release layer of the skin closure device in accordance with the fourth embodiment of the invention, leaving just the cured adhesive layer in place on the patient's forearm.

FIG. 22 is a perspective view showing the physician's or nurse's hand 21 removing the siliconised release liner 405 from the adhesive layer 402 of the skin closure film after the curable molecules in the adhesive composition of the adhesive layer 402 have been cured. After removal of the siliconised release liner 405, only the cured adhesive composition layer 402 remains on the patient's forearm 14.

As mentioned above, in the cured state, the adhesive composition of the adhesive layer 402 is transformed from its initial viscoelastic state to an elastic state. In the elastic state, the adhesive composition layer 402 remains firmly stuck to the patient's skin but, by virtue of its elasticity, the adhesive layer is able to move with the patient's skin as the patient moves. The cured adhesive composition layer is an effective barrier to bacteria. Any bacteria that remained on the surface of the patient's skin after preliminary antibacterial swabbing become immobilised in the cured adhesive composition layer and migration to the site of the wound is thereby inhibited. The cured adhesive composition layer 402 is also a mechanical barrier against dirt and other foreign particles and substances.

The cured adhesive composition layer 402 of the skin closure film remains in position on the patient's skin over the wound 15. The skin closure film is breathable and allows moisture, including sweat, to escape from the pores of the patient's skin. Moreover, the cured adhesive composition layer 402 has good water resistance and does not require special care by the patient when bathing or showering. Preferably, the cured adhesive composition layer 402 is transparent to allow inspection of the underlying skin surface without needing to remove the skin closure film.

The adhesive composition layer 402 is gradually sloughed away with the shedding of skin cells from the surface of the patient's skin as wound healing progresses.

Although the first, second, third and fourth embodiments have been described above in terms of a particular construction for the laminated product, the present invention is not limited to such a construction.

For example, at least the first carrier layer or the first release liner may have a tab that is not coated with the adhesive composition, the tab serving to facilitate handling of the laminated product so that the carrier layer or the release liner can be separated from the adhesive composition layer without the adhesive composition layer coming into contact with the physician's or nurse's fingers or gloves.

A non-adhesive-coated tab may also be provided on the second carrier layer of the wound dressing described in the first embodiment to assist in removal of the second carrier layer with the film of switched adhesive after the curable molecules in the adhesive composition layer have undergone their curing reaction to transform the adhesive composition layer from its tacky state to its non-tacky or low-tack state.

Similarly, a non-adhesive-coated tab may also be provided on the second release liner to assist in its removal from the adhesive composition layer after the curable molecules in the adhesive composition layer have undergone their curing reaction to transform the adhesive composition layer from its viscoelastic state to its elastic state.

The first release liner does not need to be formed of a light occlusive material. If the packaging for the laminated product is light occlusive, the first release liner may be transparent though, of course, the first release liner will need to be removed quickly and the laminated product will need to be applied quickly to the patient's skin if the photoinitiator in the adhesive composition layer is activated by visible light. The need for quick deployment of the laminated product is not as critical for adhesive composition layers that use a photoinitiator responsive to UV light but not responsive to visible light.

Similarly, the second release liner does not need to have a light occlusive layer. However, if the second release liner in the second, third and fourth embodiments described above consists of two layers (a light occlusive layer as well as siliconised release liners 205, 305 and 405), the layers may be stuck together using a low peel strength adhesive. As an alternative, they may be heat laminated together.

The release liners may be siliconised paper rather than siliconised plastic films.

100% transparency is not essential for the second carrier layer or the second release liner. It may be semi-transparent provided that it allows sufficient light (UV light and/or visible light) to pass through it to enable photoinitiated radical reaction of the curable molecules in the underlying adhesive composition layer.

FIFTH EMBODIMENT

A fifth embodiment of the present invention in the form of an alternative skin closure product will now be described with reference to FIGS. 23 to 25.

Figure 23:
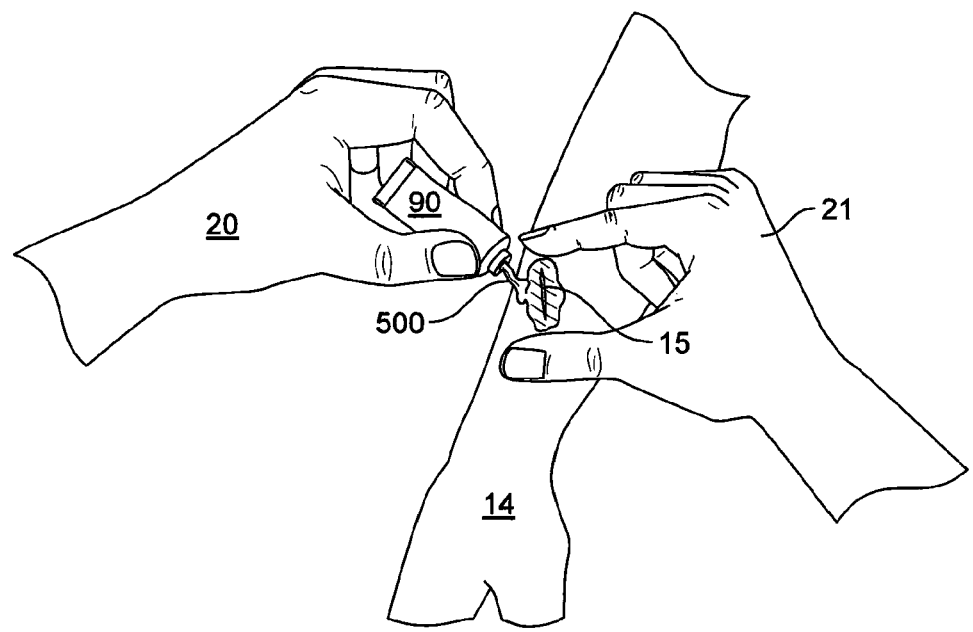
FIG. 23 is a perspective view showing a curable skin closure composition being dispensed from a tube in accordance with a fifth embodiment of the invention.

FIG. 23 is a perspective view showing a skin closure product 500 in accordance with the fourth embodiment of the invention being applied in place on a patient's forearm 14 for closing a gaping wound 15. The skin edges of the gaping wound 15 are shown being urged together by stretching the ends of the wound apart by the thumb and forefinger of the physician's or nurse's hand 21 as the skin closure product 500, in the form of a viscoelastic composition, is dispensed from a tube 90. After dispensing the composition onto the patient's skin, the physician or nurse may, if necessary, use a spatula or similar tool held in his or her free hand to spread the composition over the wound site to achieve a skin closure film 502 of substantially even thickness.

FIG. 24 is a perspective view of the skin closure film 502 in position on the skin of the patient and undergoing irradiation, in this example from a lamp 60, to effect cure of the curable molecules in the adhesive composition whilst the skin edges of the gaping wound 15 are still being urged together by the thumb and forefinger of the physician's or nurse's hand 21 stretching the ends of the wound apart. The light from the lamp 60 (UV light or visible light, preferably long wavelength UV light) initiates curing of the curable molecules in the adhesive composition. Curing of the curable molecules transforms the skin closure composition from its viscoelastic state to an elastic state.

Although FIGS. 23 and 24 show the skin edges of the wound 15 being urged together by the action of stretching the patient's skin at the ends of the wound in the longitudinal direction of the wound, it will be understood that squeezing the skin edges together may be a more suitable technique. Also, more than one hand may be needed to urge the skin edges of the wound together over the entire length of the wound. In these circumstances, a second physician or nurse may assist by dispensing the skin closure composition onto the site of the wound.

The skin closure composition in the tube 90 may contain only a minor amount of an adhesive polymer constituent, since an adhesive polymer constituent would make the skin closure composition very viscous and therefore difficult to dispense from a tube. For example, the skin closure composition may contain up to 10% by weight of an adhesive polymer constituent. Preferably, the skin closure composition contains up to 5% by weight or less of the adhesive polymer constituent. If present, the adhesive may be a hot melt acrylic material such as Nanostrength M65 or Nanostrength M75. The purpose of adding an adhesive polymer constituent is for adjustment of the viscosity of the skin closure composition. More preferably, the skin closure composition has no adhesive polymer constituent and is comprised mainly of curable molecules curable by free radical polymerization, with photoinitiator and minor incidental ingredients. The viscosity of the skin closure composition is preferably in the range 1 to 100,000 mPa·s, more preferably 100 to 20,000 mPa·s.

After curing, the skin closure film 502 in its elastic state is able to hold the skin edges of the wound 15 together without requiring the assistance of the physician's or nurse's hand 21. FIG. 25 is a perspective view of the cured skin closure film 502 in place on the patient's skin, overlying the closed wound.

As mentioned above, in the cured state, the composition of the skin closure film 502 is transformed from its initial viscoelastic state to an elastic state. In the elastic state, the skin closure film remains firmly stuck to the patient's skin. Moreover, the cured skin closure composition layer is an effective barrier to bacteria. Any bacteria that remained on the surface of the patient's skin after preliminary antibacterial swabbing become immobilised in the cured skin closure composition layer and migration to the site of the wound is thereby inhibited. The skin closure film 502 is also a mechanical barrier against dirt and other foreign particles and substances.

The skin closure film 502 thus remains in position on the patient's skin over the wound 15. The skin closure film is breathable and allows moisture to escape from the pores of the patient's skin. Moreover, the skin closure film 502 has good water resistance and does not require special care by the patient when bathing or showering. Preferably, the cured skin closure film 502 is transparent to allow inspection of the underlying skin surface without needing to remove the skin closure film. The skin closure film 502 is gradually sloughed away with the shedding of skin cells from the surface of the patient's skin as wound healing progresses.

Exposure to oxygen during curing causes the uppermost surface of the skin closure film 502 (i.e., the surface not in contact with the patient's skin) to remain slightly tacky after curing is complete. However, this slight tackiness can be counteracted by dusting the skin closure film 502 with talc.

Alternatively, the cured skin closure film 502 can be overlaid with a bacterial barrier 300 of the type described above in the discussion of the third embodiment, the curable molecules in the adhesive composition layer 302 of the bacterial barrier being cured by irradiation using UV light or visible light passing through the siliconised release layer 305 that lies over the adhesive layer 302. Curing the curable molecules in the adhesive composition layer 302 in this way avoids surface tackiness whilst the surface tackiness of the underlying skin closure film 502 helps to keep the bacterial barrier in place. As previously described, the siliconised release layer 305 is removed from the adhesive layer 302 of the bacterial barrier after the curable molecules in the adhesive composition of the adhesive layer 302 have been cured.

The combined skin closure film 502 and adhesive layer 302 gradually slough away with the shedding of skin cells from the surface of the patient's skin as wound healing progresses.

In yet another alternative to combat surface tackiness, the skin closure composition may include a component containing aliphatic thiol groups. Besides having oxygen-scavenging properties, the aliphatic thiols can also take part in the radical polymerization of the curable molecules via thiol-ene reactions. For a more effective contribution to the curing reaction, a component with two or more thiol groups could be used, such as trimethylolpropanetris(3-mercaptopropionate) or pentaerythritoltetrakis(2-mercaptoacetate). Amine synergists such as triethanol amine or ethyl-4-dimethylaminobenzoate could also be used to reduce oxygen inhibition of the radical polymerization at the exposed surface.

EXAMPLES

The invention will now be further illustrated with reference to Examples. Firstly, we will describe how exemplary oligomeric curable molecules for use in the switchable adhesive compositions of the present invention may be prepared.

Reaction 1. Formation of Polyurethane with Pendant Isocyanate Groups

In this case a diol is used to give an initial increase to the molecular weight of an isocyanate monomer. Isocyanate, catalyst and solvent were charged into a reaction vessel equipped with a stirrer and heated to 60° C. Then the diol was added slowly over a period of 1 hour and without raising the temperature above 70° C. When all of the diol had been added, a sample was removed from the reaction vessel every 30 minutes and analyzed in a GPC instrument (identified below) until no traces of the diol could be detected in the chromatogram.

Reaction 2. Synthesis of Methacrylated Oligomers

All oligomers were prepared in a similar way. The reaction was carried out at 60° C. under stirring and the reactants were added in a manner to keep the reaction temperature under 70° C. All syntheses started with the isocyanate-containing component, catalyst (if not added previously) and inhibitor in the reaction vessel, whereafter the hydroxyl containing methacrylic ester was carefully added in order to avoid a steep rise in temperature.

In cases in which two different hydroxyl containing methacrylic esters were used, the one with the higher molecular weight was added first while the low molecular hydroxyl containing methacrylic ester was added later after confirming by GPC measurements that the higher molecular hydroxyl containing methacrylic ester had completely reacted.

After all the reactants been added, the temperature was raised to 70° C. and the mixture was left under stirring for a period of two days. Then, the ethanol was added and the temperature was maintained at 70° C. for another two hours.

Examples of Synthesized Acrylate Oligomers

In the Examples below, the constituents are listed in the order:

1 Isocyanate

2 Solvent, if present

3 Catalyst

4 Dihydroxyl component, if present

5 Stabilizer for preventing premature switch during storage

6 Hydroxyl containing methacrylate ester.

7 Ethanol

8 Hydroxyl containing photoinitiator, if present

Example 1

| | Component | Amount (g) |
|---|---|---|
| 1 | Vestanate TMDI | 252.5 |
| 2 | Ethyl acetate | 105.6 |
| 3 | DBTDL | 0.173 |
| 4 | Butanediol | 44.0 |
| 5 | Irganox 1010 | 1.27 |
| 6 | Bisomer HEMA | 192.3 |
| 7 | Ethanol | 10.0 |

The synthesis was performed according to reactions 1 and 2.

Example 2

| | Component | Amount (g) |
|---|---|---|
| 1 | Desmodur N3600 | 200.2 |
| 2 | Ethyl acetate | 10.6 |
| 3 | DBTDL | 0.192 |
| 5 | Irganox 1010 | 0.89 |
| 6 | Bisomer HEMA | 144.1 |
| 7 | Ethanol | 10.0 |

The synthesis was performed according to reaction 2.

Example 3

| | Component | Amount (g) |
|---|---|---|
| 1 | Desmodur N3600 | 200.2 |
| 2 | Butyl acetate | 30.2 |
| 3 | DBTDL | 0.160 |
| 5 | Irganox 1010 | 0.87 |
| 6a | Bisomer PPM5 LI | 130.2 |
| 6b | Bisomer HPMA | 110.5 |
| 7 | Ethanol | 10.0 |

The synthesis was performed according to reaction 2.

Example 4

| | Component | Amount (g) |
|---|---|---|
| 1 | Desmodur N3900 | 200.7 |
| 2 | Butyl acetate | 30.1 |
| 3 | DBTDL | 0.24 |
| 4 | Polypropylene glycol Mn = 425 | 53.3 |
| 5 | Irganox 1010 | 0.97 |
| 6 | Bisomer HPMA | 130.6 |
| 7 | Ethanol | 10.0 |

The synthesis was performed according to reactions 1 and 2.

Example 5

| | Component | Amount (g) |
|---|---|---|
| 1 | Desmodur N3600 | 20.3 |
| 2 | Butyl acetate | 3.1 |
| 3 | DBTDL | 0.185 |
| 5 | Irganox 1010 | 0.97 |

| | Component | Amount (g) |
|---|---|---|
| 6 | Bisomer HPMA | 14.5 |
| 7 | Ethanol | 1.0 |
| 8 | Benzoin | 2.00 |

Example 5 is an example how a potentially toxic and migrating low molecular weight photoinitiator can be chemically bonded to the higher molecular weight oligomer molecule.

The syntheses was performed by charging Desmodur N3600, butyl acetate and benzoin into a reagent bottle and stirring until the benzoin was dissolved, whereafter DBTDL was added and the temperature was raised to 60° C. After establishing that all benzoin had been consumed, Bisomer HPMA was added according to reaction 2.

Switchable Adhesive Compositions Incorporating the Oligomeric Curable Molecules

Examples 6 to 10 are examples of switchable adhesive compositions in accordance with the present invention formulated to include oligomers from Examples 1 to 5 above.

In Examples 6 to 10 below, the constituents are listed in the order:

1 base adhesive(s)
2 curable molecules
3 photoinitiator
4 additional solvent, if present

Example 6

| | Component | Amount (g) |
|---|---|---|
| 1 | ATR PSA 505 | 21.2 |
| 2 | Oligomer from Example 1 | 8.80 |
| 3 | TPO-L | 0.18 |

Example 7

| | Component | Amount (g) |
|---|---|---|
| 1 | ATR PSA 505 | 22.1 |
| 2 | Oligomer from Example 2 | 7.75 |
| 3 | Irgacure 369 | 0.180 |

Example 8

| | Component | Amount (g) |
|---|---|---|
| 1 | ATR PSA 505 | 22.1 |
| 2 | Oligomer from Example 3 | 7.96 |
| 3 | Irgacure 369 | 0.184 |

Example 9

| | Component | Amount (g) |
|---|---|---|
| 1 | Aroset 1874 | 23.0 |
| 2 | Oligomer from Example 4 | 9.2 |
| 3 | Irgacure 369 | 0.21 |
| 4 | Ethyl acetate | 4.9 |

Example 10

| | Component | Amount (g) |
|---|---|---|
| 1 | ATR PSA 505 | 21.7 |
| 2 | Oligomer from example 5 | 7.7 |
| 4a | Ethanol | 3.0 |
| 4b | Ethyl acetate | 0.6 |

Preparative Details

All components in the respective Examples 6 to 10 were loaded into a sealable glass jar and mixed to a homogenous solution using a magnetic stirrer over a period of approximately 60 minutes under protection from ultraviolet sources. The resulting adhesive solution was then spread onto a carrier film using a spreader having a gauge of 150 μm and left to dry at room temperature for 10 minutes.

The adhesive coating was then further dried in a ventilated fan assisted oven at 110° C. for an additional 10 minutes. After drying, the thickness of the adhesive coating was about 50 μm.

For peeling studies, a 23 μm Hostaphan RNK 2600 (polyester) film was transferred to the exposed side of the adhesive in preparation for peel studies. This while medical film was transferred to the exposed side of the adhesive whereafter the carrier film, if present, attached to the flexible medical film was removed before performing migration and swelling tests.

Peel Force Measurements

Peel strengths were determined after a dwell time of 20 minutes using an Instron 5943 testing rig, equipped with a 100N load cell, according to FINAT test method FTM1, with the exception that high density polyethylene (HDPE) panels were used as the substrate surface and that a peeling rate of 10 mm/min crosshead speed 200 mm/s) was used in order to collect all of the necessary data within the time frame of one peel force measurement.

Adhesive switching was achieved by exposing the adhesive film (adhered to the HDPE plate) to light through the PET carrier film backing with a light intensity of approximately 5 mW/cm$^2$ from a XeLED-Ni3UV-R4-365-E27-SS lamp having a narrow spectrum around 365 nm. Switching times for the different coatings were measured as the time between the starting time of irradiation and the time when the substantially instantaneous loss of tack occurred, during a continuous peel strength test of about 1 minute (i.e., the adhesive was peeled for a period of time whilst being irradiated). Peel strengths and switching times were measured in quadruple and the average values of switch time and peel force (before and after switch) were calculated.

The results are presented below in Table 1. Where the weakest point in the adherent chain ceases to be the cohesive strength and instead changes to become the adhesive strength, the failure mode changes from cohesive failure (CF) to so-called "clean panel" (CP) indicating that no residual adhesive was left on the test plates.

Gel Permeation Chromatography (GPC)

Samples were diluted with tetrahydrofuran in a ratio of 1:100 and injected in an amount of 20 µl into the injection valve of a Waters HPLC 1515 pump using a flow rate of 1 ml/min. The instrument was equipped with Styragel HR3 and HR1 columns connected to a Waters 2414 refractive index detector. Calibration was done with polystyrene standards.

TABLE 1

Adhesive composition properties

| Example Number | Coat weight (g/m$^2$) | Peel force before switch (N/25 mm) | Peel force after switch (N/25 mm) | Switch time (seconds) | Initial peel force failure mode |
|---|---|---|---|---|---|
| 6 | 44 | 15.1 | 0.26 | 5.9 | CF |
| 7 | 55 | 26.4 | 0.21 | 3.6 | CF |
| 8 | 66 | 23.3 | 0.20 | 3.8 | CF |
| 9 | 65 | 7.4 | 0.24 | 6.1 | CP |
| 10 | 52 | 6.3 | 1.5 | 38 | CP |

Medical Film Swelling and Migration Test

Swelling and wrinkling of medical films as a result of their contact with moisture or low molecular weight components present in adhesives is a perennial problem in the medical products field. This is undesirable because it means that a medical product incorporating the medical film (e.g. adhesive dressing, surgical drape, bacterial barrier, skin closure product) may be rendered incapable of application to a patient if the wrinkling is sufficiently severe that channels are formed that would compromise the wound site.

Tests were therefore performed on the adhesive Examples 6 to 10 with different commercially available films (designated as EU29, EU31, B020-67 and Code 48938). Film EU29 is said by the manufacturers to be a shower-proof film—medical products based on this film should not swell or wrinkle when the user takes a shower. Film EU31 is a so-called "reactive" film which swells during showering, but dries out afterwards and reverts to its unwetted condition. Film B020-67 is an unreactive film that does not swell or wrinkle during showering.

In the tests, after removal of the carrier film (medical films are typically very flexible so they are usually supplied with a carrier film in order to support the otherwise flexible film), the laminate consisting of the release liner, adhesive and medical film to be tested was stored for a period of one week, whereafter wrinkling of the film was judged by eye according to Table 2 below.

TABLE 2

Numerical description of wrinkles

| | |
|---|---|
| 0 | No visible change compared to unlaminated film |
| 1− | A barely visible change |
| 1 | A visible pattern on some parts of the surface |
| 1+ | A visible pattern can be seen all over the surface |
| 2− | Fingerprint like pattern on some parts of the surface |
| 2 | Fingerprint like pattern on the whole surface |
| 3 | A distinct pattern can be seen on the whole surface |
| 4 | Distinct pattern combined with wrinkling and channels |
| 5 | Swelling, channels and wrinldes all over the surface |

Cytotoxicity Testing

Extraction Medium

Complete cell culture medium: HAM F12 with 10% foetal bovine serum and 50 µg/mL gentamycin (all supplied by Gibco).

Extraction Procedure

The extraction procedure was performed under red light conditions using a standard fluorescent light covered with red film that had been supplied by the Sponsor (A5, Encapsulite Int. Ltd, Bedfordshire, England, Internal Lumina REF_3337). All references to red light in this description of the cytotoxicity testing refer to this light source.

Test samples were cut out as 30×30 mm squares of adhesive between two release liners. One release liner was removed and the adhesive was glued to the bottom of a sterile glass beaker. Then the second liner was removed. The adhesive was then covered with 1.5 ml complete cell culture medium, corresponding to an extraction ratio of 6 cm$^2$ surface area of the test sample/ml medium. This was repeated with twelve pieces of test sample. The glass beakers were then wrapped in metal foil to protect them from light. The extraction mixture was mixed gently in an incubator set at 37° C. for 24 hours. The procedures were carried out under aseptic conditions.

At the end of the extraction period, the extract was collected under red light and used in the cytotoxicity test on the same day. The appearance of the extract could not be assessed as the procedures were performed under red light. Three dilutions of the test sample extract were tested in addition to the undiluted extract. These dilutions were 1+0.75, 1+1.5 and 1+3 (one part extract+0.75, 1.5 or 3 parts fresh culture medium, respectively).

Cells

The cells used, L929 mouse fibroblasts (ECACC No. 85011425) obtained from the European Collection of Cell Cultures, were cultured in HAM F12 medium supplemented with 10% foetal bovine serum and 50 µg/mL gentamycin.

The L929 cells grew as monolayer cultures, which were sub-cultured by re-suspension using trypsin-EDTA, dilution and then reseeding. The cells were cultured in sterile plastic flasks and incubated at 37° C. in a humidified atmosphere of 5% carbon dioxide in air.

Frozen stock cultures were kept in a liquid nitrogen tank at −196° C. New stock cultures were made periodically when necessary: confluent cultures were treated with trypsin-EDTA solution, the cells were resuspended in fresh medium, and dimethyl sulphoxide was added (10% v/v). Vials of the cell suspension were frozen slowly in a freezer (−80° C.), then transferred to a liquid nitrogen tank. The cells were thawed in a water bath at 37° C. when required.

Before new stock cultures were used in assays, the cells were checked for general appearance and growth characteristics.

Cytotoxicity Assay

On the day before the test, continuously mixed suspensions of L929 cells were used to seed 24-well microtitre plates. Just before the test, the cultures were checked to ensure that the cells had normal morphology and were sub-confluent (over 80% and under 100% confluent). Three cultures were treated by replacing the normal medium with the test sample extract. Three dilutions of the test sample extract (1 part extract+0.75 parts fresh cell culture medium, 1+1.5 and 1+3) were also tested in three cultures each to characterise any cytotoxicity observed. The cell cultures were protected from light using metal foil throughout the treatment period until the level of cytotoxicity was scored.

A red light was used when necessary for treatment and addition of Neutral Red stain.

Three positive control cultures were treated with a 0.2 mg/ml solution of sodium lauryl sulphate (SLS, sodium dodecyl sulphate) (a solution of SLS was prepared at 20 mg/mL in sterile purified water and this was diluted 100-fold with cell culture medium to a final SLS concentration of 0.2 mg/mL just before the cells were treated). Three negative control cultures were treated with an extract of high density polypropylene (PP, NUNC 4.5 mL cryotubes) prepared in cell culture medium at 37° C. for 24 hours using an extraction ratio of 6 cm$^2$/mL. Three untreated control cultures (treated with cell culture medium which had been processed in the same way as the test item extract) were included.

The treated cultures were incubated at about 37° C. in a humidified atmosphere of 5% carbon dioxide in air for 48 hours. At the end of this treatment period, the cultures were inspected with an inverted microscope. Neutral Red stain (125 μL) was added to the cultures 1-2 hours before the inspection in order to distinguish clearly between live and dead cells. The general appearance of the monolayer and the approximate percentage of live cells were recorded for each culture using Table 3 below (from ISO10993-5 Table 1 and USP <87> Table 2) as guidance.

TABLE 3

Cytotoxicity Assessment

| Grade | Reactivity | Condition of Cultures |
|---|---|---|
| 0 | None | Discrete intracytoplasmic granules; no cell lysis. |
| 1 | Slight | Not more than 20% of the cells are round, loosely attached, and without intracytoplasmic granules; occasional lysed cells are present. |
| 2 | Mild | Not more than 50% of the cells are round and devoid of intracyto-plasmic granules; no extensive cell lysis and empty areas between cells. |
| 3 | Moderate | Not more than 70% of the cell layers contain rounded cells or are lysed. |
| 4 | Severe | Nearly complete destruction of the cell layers. |

The test sample is considered to pass the test if the cytotoxicity grade is 2 or less.

Table 4 below is a combined table of adhesive composition molecular weights, cytotoxicity and medical film wrinkling properties for Examples 6 to 10. Table 4 shows that the adhesive compositions having the lighter molecular weight oligomeric curable groups (Example 6 especially, and Example 7) performed less well with the film types EU29, EU31 and Code 48938, whereas the adhesive compositions having the higher molecular weight oligomeric curable groups (Examples 8 and 9) performed well with all film types tested.

These results show that, just as with conventional adhesives, care must be taken when selecting a medical film for use with the switchable adhesives of the present invention.

TABLE 4

Adhesive composition molecular weight, cytotoxicity and medical film wrinkling properties

| Example Number | Number average molecular weight of oligomer, $M_n$ | Weight average molecular weight of oligomer, $M_w$ | Double bond equivalents per kilogram | Cytotoxicity result | Film wrinkling severity according to Table 2 scale | | | |
|---|---|---|---|---|---|---|---|---|
| | | | | | EU29 | EU31 | B020-67 | Code 48938 |
| 6 | 675 | 841 | 2.9 | 0 | 5 | 4 | 0 | 5 |
| 7 | 1024 | 1120 | 3.2 | 0 | 3 | 3 | * | * |
| 8 | 1311 | 1585 | 2.5 | 0 | 3 | 1− | 0 | 1 |
| 9 | 1654 | 4082 | 2.2 | 0 | 1− | 0 | 0 | 0 |
| 10 | 1107 | 1223 | 3.0 | 0 | * | * | * | * |

* Not tested

COMPARATIVE EXAMPLES

The following comparative examples are examples of switchable adhesives containing commercially available oligomers which are stated by the manufactures to be without any CLP Regulation ("Classification, Labelling and Packaging") hazards and to be of low skin irritancy. It should be noted that the removal of residual monomers in the drying process of the adhesive and the incorporation of the commercially available oligomers in the base adhesive polymer are expected to improve their biocompatibility.

In the Examples below, the constituents are listed in the order:

1 base adhesive
2 curable molecules
3 photoinitiator
4 radical stabilizer

Comparative Example A

| | Component | Amount (g) |
|---|---|---|
| 1 | Aroset 1450 Z 40 | 100.6 |
| 2 | CN 925 | 28.5 |
| 3 | Irgacure 784 | 0.78 |
| 4 | Irganox 1010 | 0.10 |

Comparative Example B

| | Component | Amount (g) |
|---|---|---|
| 1 | Aroset 1450 Z 40 | 40.0 |
| 2 | CN 965 | 12.6 |
| 3 | Irgacure 784 | 0.45 |
| 4 | Irganox 1010 | 0.020 |

Comparative Example C

| | Component | Amount (g) |
|---|---|---|
| 1 | Aroset 1450 Z 40 | 22.0 |
| 2 | Genomer 4256 | 6.8 |
| 3 | Irgacure 784 | 0.14 |
| 4 | Irganox 1010 | 0.022 |

Comparative Example D

| | Component | Amount (g) |
|---|---|---|
| 1 | Aroset 1450 Z 40 | 24.8 |
| 2 | Epoxy methacrylate 97-053 | 6.9 |
| 3 | Irgacure 784 | 0.14 |
| 4 | Irganox 1010 | 0.020 |

The cytotoxicity of the Comparative Examples A to D measured according to cytotoxicity tests complying with the methods described in ISO 10993-5 standard for the eluation test is displayed in Table 5 below. Note that undiluted examples all exhibited cytotoxicity. To determine whether less concentrated examples would show more favourable cytotoxicity, the adhesive composition extracts were diluted. In the table, dilution ratio indicates to what extent the extract was diluted before performing the cytotoxicity test. The ratio extract:culture media is tabulated. It should be noted that it is only the undiluted result, 1:0, that decides if the sample has passed the test or not. All of the Comparative Examples exhibited the maximum possible cytotoxicity score of 4 when undiluted.

TABLE 5

Comparative Example cytotoxicity

| Comparative Example | Dilution ratio | | | | |
|---|---|---|---|---|---|
| | Undiluted | 1:0.75 | 1:1.5 | 1:3 | 1:6 |
| A | 4 | * | 4 | 3 | * |
| B | 4 | * | 4 | 4 | 3 |
| C | 4 | * | 4 | 4 | 4 |
| D | 4 | 2 | 0-1 | 0 | * |

* Not tested

TABLE 6

Table of Suppliers

| Component | Description | Company |
|---|---|---|
| Vestanat TMDI | Trimethyl hexamethylene diisocyanate | Evonik Industries AG |
| Vestanat T 1890 | Isophorone polyisocyanate diluted with 30% butyl acetate | Evonik Industries AG |
| Desmodur N 3600 | Hexamethylene polyisocyanate (isocyanurate) | Bayer Material Science AG |
| Desmodur N 3900 | Hexamethylene polyisocyanate (iminooxadiazindione) | Bayer Material Science AG |
| Bisomer HPMA | Hydroxypropyl methacrylate | GEO Specialty Chemicals UK Ltd |
| Bisomer HEMA | Hydroxyethyl methacrylate | GEO Specialty Chemicals UK Ltd |
| Bisomer PPM5 LI | Polypropyleneglycol monomethacrylate | GEO Specialty Chemicals UK Ltd |
| Decanediol | Diol | Sigma-Aldrich |
| Butandiol | Diol | Sigma-Aldrich |
| Polypropyleneglycol Mn 425 | Diol | Sigma-Aldrich |
| Irganox 1010 | Pentaerythritol Tetralds(3-(3,5-di-tert-butyl-4-hydroxyphenyl) propionate | BASF AG |
| Irgacure 369 | 2-Benzyl-2-dimethylamino-1-(4-morpholinophenyl)-butanone-1 | BASF AG |
| Irgacure 784 | Bis(.eta.5-2,4-cylcopentadien-1-yl)-bis(2,6-difluoro-3-(1H-pyrrol-1-yl)-phenyl) titanium | BASF AG |
| TPO-L | UV initiator | Rahn AG |
| ATR PSA 505 | Self-cured acrylic copolymer. | ATR Chemicals SA |
| Aroset 1450 Z 40 | Acrylic copolymer | Ashland Inc. |
| Aroset 1874 | Acrylic copolymer | Ashland Inc. |
| CN 927 | Modified aliphatic urethane tetraacrylate | Sartomer |
| CN 965 | Aliphatic urethane diacrylate | Sartomer |
| Genomer 4256 | Aliphatic urethane methacrylate | Rahn AG |
| Epoxy methacrylate 97-053 | Epoxy methacrylate | Rahn AG |
| EU29 | Medical film | Smith&Nephew Extruded Films Ltd |
| EU31 | Medical film | Smith&Nephew Extruded Films Ltd |
| B020-67, 20 μm | Medical film | Gergonne Industri |
| Code 48938 | Medical film | Shanghai ISO Medical Products Co. Ltd |
| XeLED-Ni3UV-R4-365-E27-SS | LED ultra violet light source | Xenopus Electronix |

TABLE 6-continued

Table of Suppliers

| Component | Description | Company |
|---|---|---|
| HDPE panels | Panels for peel test measurements | ChemInstrument Inc. |
| Hostaphan RNK 2600 | Polyester film | Mitsubishi Polyester Film GmbH |

What is claimed is:

1. A switchable adhesive composition comprising a mixture of a pressure sensitive adhesive component, curable molecules that are curable by free radical polymerization, a photoinitiator, and a stabiliser, wherein the curable molecules are oligomers of at least one of the following formulae (I) to (VII):

$$CA(BA)_nC \qquad (I)$$

where n is 0 or an integer from 1 to 100,
A is a diisocyanate, a diepoxide, a diol or a dicarboxylic acid;
B is a diol when A is a diisocyanate or a dicarboxylic acid; B is a dicarboxylic acid when A is a diepoxide or a diol;
C is a hydroxyl containing methacrylate ester when A is a diisocyanate or a dicarboxylic acid; C is methacrylic acid when A is a diepoxide or a diol;

$$C_2E(BCE)_nC \qquad (II)$$

where n is 0 or an integer from 1 to 100,
E is a tri-isocyanate, a triepoxide, a triol or a tricarboxylic acid;
B is a diol when E is a tri-isocyanate or a tricarboxylic acid; B is a dicarboxylic acid when E is a triepoxide or a triol;
C is a hydroxyl containing methacrylate ester when E is a triisocyanate or a tricarboxylic acid; C is methacrylic acid when E is a triepoxide or a triol;

$$E_{(2n+1)}F_nC_{(3n+3)} \qquad (III)$$

where n is 0 or an integer from 1 to 100,
E is a tri-isocyanate, a triepoxide, a triol or a tricarboxylic acid;
F is a triol when E is a tri-isocyanate or a tricarboxylic acid; F is a tricarboxylic acid when E is a triepoxide or a triol;
C is a hydroxyl containing methacrylate ester when E is a triisocyanate or a tricarboxylic acid; C is methacrylic acid when E is a triepoxide or a triol;

$$G_{(n+1)}B_nC_{(2n+4)} \qquad (IV)$$

where n is 0 or an integer from 1 to 100,
G is a tetra-isocyanate or a tetra-carboxylic acid;
B is a diol;
C is a hydroxyl containing methacrylate ester;

$$DC_3 \qquad (V)$$

where D is a symmetrical isocyanurate trimeric ring structure or an asymmetric trimeric iminooxadiazinedione ring structure consisting of three diisocyanate molecules, or a linear trimeric biuret or allophanate structure,
C is a hydroxyl containing methacrylate ester;

$$H_xC_{(x+2)} \qquad (VI)$$

where x is 1, 2, 3, 4, 5 or 6,
$H_x$ is x symmetrical isocyanurate trimeric ring structures or x asymmetric trimeric iminooxadiazinedione ring structures consisting of three diisocyanate molecules, or x linear trimeric biuret or allophanate structures linked together in a homopolymer,
C is a hydroxyl containing methacrylate ester;

$$I_yC_y \qquad (VII)$$

where y is 2, 3, 4, 5, 6, 7, 8, or 9,
$I_y$ is polyisocyanate, a polyepoxide, a polyol or a polycarboxylic acid with y numbers of functionalities;
C is a hydroxyl containing methacrylate ester when I is a polyisocyanate or a polycarboxylic acid; C is methacrylic acid when I is a polyepoxide or a polyol;
wherein the oligomers have a weight average molecular weight in the range from 1,500 to 10,000 dalton.

2. The switchable adhesive composition of claim 1, wherein the adhesive composition comprises a mixture, in proportions by weight based on the weight of the composition, of:
10% to 95% of a pressure sensitive adhesive component;
10% to 85% of curable molecules; and
0.1% to 10% of photoinitiator, and
0.01% to 2% of stabiliser;
the weight proportion of the pressure sensitive adhesive component being calculated on the basis of its dry weight.

3. The switchable adhesive composition of claim 1, wherein the adhesive composition comprises a mixture, in proportions by weight based on the weight of the composition, of:
20% to 75% of pressure sensitive adhesive component;
20% to 75% of curable molecules; and
0.1% to 5% of photoinitiator, and
0.1% to 1% of stabiliser;
the weight proportion of the pressure sensitive adhesive component being calculated on the basis of its dry weight.

4. The switchable adhesive composition of claim 1, wherein the adhesive composition comprises a mixture, in proportions by weight based on the weight of the composition, of:
40% to 70% of pressure sensitive adhesive component;
30% to 60% of curable molecules; and
0.5% to 2% of photoinitiator, and
0.1% to 0.5% of stabiliser;
the weight proportion of the pressure sensitive adhesive component being calculated on the basis of its dry weight.

5. The switchable adhesive composition of claim 1, wherein the pressure sensitive adhesive component is a mixture.

6. The switchable adhesive composition of claim 1, wherein the curable molecules have multiple functionality.

7. The switchable adhesive composition of claim 1, wherein the photoinitiator is selected from the group consisting of: benzoin, ethyl benzoin, isopropyl benzoin, 2,4, 6-trimethylbenzoyl diphenylphosphine oxide, 2-Benzyl-2-dimethylamino-1-(4-morpholinophenyl)-butanone-1, 2-Hydroxy-2-methyl-1-phenyl-propan-1-one, Bis(2,4,6-trimethyl benzoyl)-phenylphosphineoxide, 2-Methyl-1[4-(methylthio)phenyl]-2-morpholino-propan-1-one, 1-[9-ethyl-6-(2-methylbenzoyl)-9H-carbazol-3-yl]-, 1-(O-acetyloxime), 2-Hydroxy-1-{4-[4-(2-hydroxy-2-methyl-propionyl)-benzyl]-phenyl}-2-methyl-propan-1-one, 4,4'-bis (diethyl amino)benzophenone, 2-chlorothioxanthen-9-one, 4-(dimethyl-amino)benzophenone, 2,5-dimethylbenzophenone, 4-hydroxybenzophenene, methylbenzoylformate, Phenanthrenequinone, 2-ethylanthraquinone, Bis(.eta.5-2,4-cylcopentadien-1-yl)-bis(2,6-difluoro-3-(1H-pyrrol-1-yl)-phenyl) titanium; Bis(2,4,6-trimethyl-benzoyl)-phenylphosphineoxide; camphor-quinone in combination with a tertiary amine; 2,4-Diethylthioxanthone in combination with a tertiary amine, and Isopropylthioxanthone combined with a tertiary amine.

8. The switchable adhesive composition of claim 1, wherein the photoinitiator is reactive to long wavelength UV light.

9. The switchable adhesive composition of claim 1, wherein the photoinitiator is reactive to visible light.

10. The switchable adhesive composition of claim 1, wherein the pressure sensitive adhesive component and the curable molecules are mutually soluble when dry.

11. The switchable adhesive composition of claim 1, wherein no visible wrinkling is observed in a medical film to which the switchable adhesive composition has been applied, after one week in contact with the switchable adhesive composition.

12. A method of making a switchable adhesive composition comprising a mixture of a pressure sensitive adhesive component, curable molecules that are curable by free radical polymerization, a photoinitiator, and a stabiliser, the method comprising:
(i) stirring together the pressure sensitive adhesive component, the curable molecules, the photoinitiator and the stabiliser in darkness or under red light conditions;
(ii) coating the resulting mixture onto a carrier film;
(iii) allowing the coated mixture to dry; and
(iv) applying a second carrier film to the exposed surface of the dried spread mixture;
wherein the curable molecules are oligomers of at least one of the following formulae (I) to (VII):

$$CA(BA)_nC \tag{I}$$

where n is 0 or an integer from 1 to 100,
A is a diisocyanate, a diepoxide, a diol or a dicarboxylic acid;
B is a diol when A is a diisocyanate or a dicarboxylic acid; B is a dicarboxylic acid when A is a diepoxide or a diol;
C is a hydroxyl containing methacrylate ester when A is a diisocyanate or a dicarboxylic acid; C is methacrylic acid when A is a diepoxide or a diol;

$$C_2E(BCE)_nC \tag{II}$$

where n is 0 or an integer from 1 to 100,
E is a tri-isocyanate, a triepoxide, a triol or a tricarboxylic acid;
B is a diol when E is a tri-isocyanate or a tricarboxylic acid; B is a dicarboxylic acid when E is a triepoxide or a triol;
C is a hydroxyl containing methacrylate ester when E is a triisocyanate or a tricarboxylic acid; C is methacrylic acid when E is a triepoxide or a triol;

$$E_{(2n+1)}F_nC_{(3n+3)} \tag{III}$$

where n is 0 or an integer from 1 to 100,
E is a tri-isocyanate, a triepoxide, a triol or a tricarboxylic acid;
F is a triol when E is a tri-isocyanate or a tricarboxylic acid; F is a tricarboxylic acid when E is a triepoxide or a triol;
C is a hydroxyl containing methacrylate ester when E is a triisocyanate or a tricarboxylic acid; C is methacrylic acid when E is a triepoxide or a triol;

$$G_{(n+1)}B_nC_{(2n+4)} \tag{IV}$$

where n is 0 or an integer from 1 to 100,
G is a tetra-isocyanate or a tetra-carboxylic acid;
B is a diol;
C is a hydroxyl containing methacrylate ester;

$$DC_3 \tag{V}$$

where D is a symmetrical isocyanurate trimeric ring structure or an asymmetric trimeric iminooxadiazinedione ring structure consisting of three diisocyanate molecules, or a linear trimeric biuret or allophanate structure,
C is a hydroxyl containing methacrylate ester;

$$H_xC_{(x+2)} \tag{VI}$$

where x is 1, 2, 3, 4, 5 or 6,
$H_x$ is x symmetrical isocyanurate trimeric ring structures or x asymmetric trimeric iminooxadiazinedione ring structures consisting of three diisocyanate molecules, or x linear trimeric biuret or allophanate structures linked together in a homopolymer,
C is a hydroxyl containing methacrylate ester;

$$I_yC_y \tag{VII}$$

where y is 2, 3, 4, 5, 6, 7, 8, or 9,
$I_y$ is polyisocyanate, a polyepoxide, a polyol or a polycarboxylic acid with y numbers of functionalities;
C is a hydroxyl containing methacrylate ester when I is a polyisocyanate or a polycarboxylic acid; C is carboxylic acid when I is a polyepoxide or a polyol;
wherein the oligomers have a weight average molecular weight in the range from 1,500 to 10,000 dalton.

13. The method of claim 12, wherein the pressure sensitive adhesive component, the curable molecules, the photoinitiator and the stabiliser are stirred together for 30 to 60 minutes.

14. The method of claim 12, wherein the stirring is carried out at room temperature.

15. The method of claim 12, wherein the drying step (iii) is carried out at room temperature.

16. The method of claim 12, wherein the drying step (iii) comprises drying the coated mixture at room temperature for about 10 minutes followed by oven drying at 80-150° C. for 3 to 10 minutes.

17. The method of claim 12, wherein at least one of the carrier films is coated with a silicone release agent.

18. A medical skin covering having a switchable adhesive composition comprising a mixture of a pressure sensitive adhesive component, curable molecules that are curable by free radical polymerization, a photoinitiator, and a stabiliser, wherein the curable molecules are oligomers of at least one of the following formulae (I) to (VII):

$$CA(BA)_nC \tag{I}$$

where n is 0 or an integer from 1 to 100,
A is a diisocyanate, a diepoxide, a diol or a dicarboxylic acid;

B is a diol when A is a diisocyanate or a dicarboxylic acid;
B is a dicarboxylic acid when A is a diepoxide or a diol;
C is a hydroxyl containing methacrylate ester when A is a diisocyanate or a dicarboxylic acid; C is methacrylic acid when A is a diepoxide or a diol;

$$C_2E(BCE)_nC \quad (II)$$

where n is 0 or an integer from 1 to 100,
E is a tri-isocyanate, a triepoxide, a triol or a tricarboxylic acid;
B is a diol when E is a tri-isocyanate or a tricarboxylic acid; B is a dicarboxylic acid when E is a triepoxide or a triol;
C is a hydroxyl containing methacrylate ester when E is a triisocyanate or a tricarboxylic acid; C is methacrylic acid when E is a triepoxide or a triol;

$$E_{(2n+1)}F_nC_{(3n+3)} \quad (III)$$

where n is 0 or an integer from 1 to 100,
E is a tri-isocyanate, a triepoxide, a triol or a tricarboxylic acid;
F is a triol when E is a tri-isocyanate or a tricarboxylic acid; F is a tricarboxylic acid when E is a triepoxide or a triol;
C is a hydroxyl containing methacrylate ester when E is a triisocyanate or a tricarboxylic acid; C is methacrylic acid when E is a triepoxide or a triol;

$$G_{(n+1)}B_nC_{(2n+4)} \quad (IV)$$

where n is 0 or an integer from 1 to 100,
G is a tetra-isocyanate or a tetra-carboxylic acid;
B is a diol;
C is a hydroxyl containing methacrylate ester;

$$DC_3 \quad (V)$$

where D is a symmetrical isocyanurate trimeric ring structure or an asymmetric trimeric iminooxadiazinedione ring structure consisting of three diisocyanate molecules, or a linear trimeric biuret or allophanate structure,
C is a hydroxyl containing methacrylate ester;

$$H_xC_{(x+2)} \quad (VI)$$

where x is 1, 2, 3, 4, 5 or 6,
$H_x$ is x symmetrical isocyanurate trimeric ring structures or x asymmetric trimeric iminooxadiazinedione ring structures consisting of three diisocyanate molecules, or x linear trimeric biuret or allophanate structures linked together in a homopolymer, C is a hydroxyl containing methacrylate ester;

$$I_yC_y \quad (VII)$$

where y is 2, 3, 4, 5, 6, 7, 8, or 9,
$I_y$ is polyisocyanate, a polyepoxide, a polyol or a polycarboxylic acid with y numbers of functionalities;
C is a hydroxyl containing methacrylate ester when I is a polyisocyanate or a polycarboxylic acid; C is methacrylic acid when I is a polyepoxide or a polyol;
wherein the oligomers have a weight average molecular weight in the range from 1,500 to 10,000 dalton.

19. The medical skin covering of claim 18, wherein the medical skin covering is an adhesive dressing including an absorbent wound pad.

20. The medical skin covering of claim 18, wherein the medical skin covering is a surgical incision drape.

21. The medical skin covering of claim 18, wherein the medical skin covering is a bacterial barrier for covering a wound, the bacterial barrier having no absorbent wound pad.

22. The medical skin covering of claim 18, wherein the medical skin covering is a skin closure device for closing together the edges of a wound.

23. The medical skin covering of claim 18, further comprising a layer of said switchable adhesive composition disposed between a first carrier film and a second carrier film wherein at least one of the carrier films includes a light occlusive layer on the surface of the carrier film remote from the adhesive composition.

24. The medical skin covering of claim 23, wherein the carrier films have a low surface energy relative to skin so that the adhesive composition adheres preferentially to skin.

25. A method of preparing a site for surgical incision using a surgical incision drape comprising a layer of switchable adhesive composition disposed between a first carrier film and a second carrier film wherein at least one of the carrier films includes a light occlusive layer on the surface of the carrier film remote from the adhesive composition, and wherein the carrier films have a low surface energy relative to skin so that the adhesive composition adheres preferentially to skin, the method comprising:
  (i) removing the first carrier film from the surgical incision drape to expose one surface of the adhesive composition layer;
  (ii) placing the exposed surface of the adhesive composition layer on a patient's skin at the intended site for surgical incision;
  (iii) subjecting the adhesive composition layer to visible light or UV irradiation through the second carrier film to effect cure of curable molecules in the adhesive composition; and
  (iv) after curing of the curable molecules in the adhesive composition, removing the second carrier film to expose the other surface of the cured adhesive composition layer;
wherein the curable molecules are oligomers of at least one of the following formulae (I) to (VII):

$$CA(BA)_nC \quad (I)$$

where n is 0 or an integer from 1 to 100,
A is a diisocyanate, a diepoxide, a diol or a dicarboxylic acid;
B is a diol when A is a diisocyanate or a dicarboxylic acid; B is a dicarboxylic acid when A is a diepoxide or a diol;
C is a hydroxyl containing methacrylate ester when A is a diisocyanate or a dicarboxylic acid; C is methacrylic acid when A is a diepoxide or a diol;

$$C_2E(BCE)_nC \quad (II)$$

where n is 0 or an integer from 1 to 100,
E is a tri-isocyanate, a triepoxide, a triol or a tricarboxylic acid;
B is a diol when E is a tri-isocyanate or a tricarboxylic acid; B is a dicarboxylic acid when E is a triepoxide or a triol;
C is a hydroxyl containing methacrylate ester when E is a triisocyanate or a tricarboxylic acid; C is a methacrylic acid when E is a triepoxide or a triol;

$$E_{(2n+1)}F_nC_{(3n+3)} \quad (III)$$

where n is 0 or an integer from 1 to 100,
E is a tri-isocyanate, a triepoxide, a triol or a tricarboxylic acid;
F is a triol when E is a tri-isocyanate or a tricarboxylic acid; F is a tricarboxylic acid when E is a triepoxide or a triol;

C is a hydroxyl containing methacrylate ester when E is a triisocyanate or a tricarboxylic acid; C is methacrylic acid when E is a triepoxide or a triol;

$$G_{(n+1)}B_nC_{(2n+4)} \quad (IV)$$

where n is 0 or an integer from 1 to 100,
G is a tetra-isocyanate or a tetra-carboxylic acid;
B is a diol;
C is a hydroxyl containing methacrylate ester;

$$DC_3 \quad (V)$$

where D is a symmetrical isocyanurate trimeric ring structure or an asymmetric trimeric iminooxadiazinedione ring structure consisting of three diisocyanate molecules, or a linear trimeric biuret or allophanate structure,
C is a hydroxyl containing methacrylate ester;

$$H_xC_{(x+2)} \quad (VI)$$

where x is 1, 2, 3, 4, 5 or 6,
$H_x$ is x symmetrical isocyanurate trimeric ring structures or x asymmetric trimeric iminooxadiazinedione ring structures consisting of three diisocyanate molecules, or x linear trimeric biuret or allophanate structures linked together in a homopolymer,
C is a hydroxyl containing methacrylate ester;

$$I_yC_y \quad (VII)$$

where y is 2, 3, 4, 5, 6, 7, 8, or 9,
$I_y$ is polyisocyanate, a polyepoxide, a polyol or a polycarboxylic acid with y numbers of functionalities;
C is a hydroxyl containing methacrylate ester when I is a polyisocyanate or a polycarboxylic acid; C is a methacrylic acid when I is a polyepoxide or a polyol;
wherein the oligomers have a weight average molecular weight in the range from 1,500 to 10,000 dalton.

26. A method of covering a wound using a bacterial barrier comprising a layer of switchable adhesive composition disposed between a first carrier film and a second carrier film wherein at least one of the carrier films includes a light occlusive layer on the surface of the carrier film remote from the adhesive composition, and wherein the carrier films have a low surface energy relative to skin so that the adhesive composition adheres preferentially to skin, the method comprising:
(i) removing the first carrier film from the bacterial barrier to expose one surface of the adhesive composition layer;
(ii) placing the exposed surface of the adhesive composition layer on a patient's skin over the wound;
(iii) subjecting the adhesive composition layer to visible light or UV irradiation through the second carrier film to effect cure of curable molecules in the adhesive composition; and
(iv) after curing of the curable molecules in the adhesive composition, removing the second carrier film to expose the other surface of the cured adhesive composition layer;
wherein the curable molecules are oligomers of at least one of the following formulae (I) to (VII):

$$CA(BA)_nC \quad (I)$$

where n is 0 or an integer from 1 to 100,
A is a diisocyanate, a diepoxide, a diol or a dicarboxylic acid;
B is a diol when A is a diisocyanate or a dicarboxylic acid; B is a dicarboxylic acid when A is a diepoxide or a diol;
C is a hydroxyl containing methacrylate ester when A is a diisocyanate or a dicarboxylic acid; C is methacrylic acid when A is a diepoxide or a diol;

$$C_2E(BCE)_nC \quad (II)$$

where n is 0 or an integer from 1 to 100,
E is a tri-isocyanate, a triepoxide, a triol or a tricarboxylic acid;
B is a diol when E is a tri-isocyanate or a tricarboxylic acid; B is a dicarboxylic acid when E is a triepoxide or a triol;
C is a hydroxyl containing methacrylate ester when E is a triisocyanate or a tricarboxylic acid; C is methacrylic acid when E is a triepoxide or a triol;

$$E_{(2n+1)}F_nC_{(3n+3)} \quad (III)$$

where n is 0 or an integer from 1 to 100,
E is a tri-isocyanate, a triepoxide, a triol or a tricarboxylic acid;
F is a triol when E is a tri-isocyanate or a tricarboxylic acid; F is a tricarboxylic acid when E is a triepoxide or a triol;
C is a hydroxyl containing methacrylate ester when E is a triisocyanate or a tricarboxylic acid; C is methacrylic acid when E is a triepoxide or a triol;

$$G_{(n+1)}B_nC_{(2n+4)} \quad (IV)$$

where n is 0 or an integer from 1 to 100,
G is a tetra-isocyanate or a tetra-carboxylic acid;
B is a diol;
C is a hydroxyl containing methacrylate ester;

$$DC_3 \quad (V)$$

where D is a symmetrical isocyanurate trimeric ring structure or an asymmetric trimeric iminooxadiazinedione ring structure consisting of three diisocyanate molecules, or a linear trimeric biuret or allophanate structure,
C is a hydroxyl containing methacrylate ester;

$$H_xC_{(x+2)} \quad (VI)$$

where x is 1, 2, 3, 4, 5 or 6,
$H_x$ is x symmetrical isocyanurate trimeric ring structures or x asymmetric trimeric iminooxadiazinedione ring structures consisting of three diisocyanate molecules, or x linear trimeric biuret or allophanate structures linked together in a homopolymer,
C is a hydroxyl containing methacrylate ester;

$$I_yC_y \quad (VII)$$

where y is 2, 3, 4, 5, 6, 7, 8, or 9,
$I_y$ is polyisocyanate, a polyepoxide, a polyol or a polycarboxylic acid with y numbers of functionalities;
C is a hydroxyl containing methacrylate ester when I is a polyisocyanate or a polycarboxylic acid; C is methacrylic acid when I is a polyepoxide or a polyol;
and wherein the oligomers have a weight average molecular weight in the range from 1,500 to 10,000 dalton.

27. A method of closing the edges of a wound using a skin closure device comprising a layer of switchable adhesive composition disposed between a first carrier film and a second carrier film wherein at least one of the carrier films includes a light occlusive layer on the surface of the carrier film remote from the adhesive composition, and wherein the carrier films have a low surface energy relative to skin so that the adhesive composition adheres preferentially to skin, the method comprising:
  (i) removing the first carrier film from the skin closure device to expose one surface of the adhesive composition layer;
  (ii) placing one end of the exposed surface of the adhesive composition layer on a patient's skin in the vicinity of one end of the wound;
  (iii) bringing the edges of the wound together and progressively applying the adhesive composition layer along said wound from said one end to the other end of the wound;
  (iv) subjecting the adhesive composition layer to visible light or UV irradiation through the second carrier film to effect cure of curable molecules in the adhesive composition; and
  (iv) after curing of the curable molecules in the adhesive composition, removing the second carrier film to expose the other surface of the cured adhesive composition layer;
  wherein the curable molecules are oligomers of at least one of the following formulae (I) to (VII):

$$CA(BA)_nC \qquad (I)$$

where n is 0 or an integer from 1 to 100,
A is a diisocyanate, a diepoxide, a diol or a dicarboxylic acid;
B is a diol when A is a diisocyanate or a dicarboxylic acid; B is a dicarboxylic acid when A is a diepoxide or a diol;
C is a hydroxyl containing methacrylate ester when A is a diisocyanate or a dicarboxylic acid; C is methacrylic acid when A is a diepoxide or a diol;

$$C_2E(BCE)_nC \qquad (II)$$

where n is 0 or an integer from 1 to 100,
E is a tri-isocyanate, a triepoxide, a triol or a tricarboxylic acid;
B is a diol when E is a tri-isocyanate or a tricarboxylic acid; B is a dicarboxylic acid when E is a triepoxide or a triol;
C is a hydroxyl containing methacrylate ester when E is a triisocyanate or a tricarboxylic acid; C is methacrylic acid when E is a triepoxide or a triol;

$$E_{(2n+1)}F_nC_{(3n+3)} \qquad (III)$$

where n is 0 or an integer from 1 to 100,
E is a tri-isocyanate, a triepoxide, a triol or a tricarboxylic acid;
F is a triol when E is a tri-isocyanate or a tricarboxylic acid; F is a tricarboxylic acid when E is a triepoxide or a triol;
C is a hydroxyl containing methacrylate ester when E is a triisocyanate or a tricarboxylic acid; C is methacrylic acid when E is a triepoxide or a triol;

$$G_{(n+1)}B_nC_{(2n+4)} \qquad (IV)$$

where n is 0 or an integer from 1 to 100,
G is a tetra-isocyanate or a tetra-carboxylic acid;
B is a diol;
C is a hydroxyl containing methacrylate ester;

$$DC_3 \qquad (V)$$

where D is a symmetrical isocyanurate trimeric ring structure or an asymmetric trimeric iminooxadiazinedione ring structure consisting of three diisocyanate molecules, or a linear trimeric biuret or allophanate structure,
C is a hydroxyl containing methacrylate ester;

$$H_xC_{(x+2)} \qquad (VI)$$

where x is 1, 2, 3, 4, 5 or 6,
$H_x$ is x symmetrical isocyanurate trimeric ring structures or x asymmetric trimeric iminooxadiazinedione ring structures consisting of three diisocyanate molecules, or x linear trimeric biuret or allophanate structures linked together in a homopolymer,
C is a hydroxyl containing methacrylate ester;

$$I_yC_y \qquad (VII)$$

where y is 2, 3, 4, 5, 6, 7, 8, or 9,
$I_y$ is polyisocyanate, a polyepoxide, a polyol or a polycarboxylic acid with y numbers of functionalities;
C is a hydroxyl containing methacrylate ester when I is a polyisocyanate or a polycarboxylic acid; C is methacrylic acid when I is a polyepoxide or a polyol;
wherein the oligomers have a weight average molecular weight in the range from 1,500 to 10,000 dalton.

28. The method of claim 25, wherein said step of subjecting the adhesive composition layer to visible light or UV irradiation to effect cure of the curable molecules in the adhesive composition comprises removing an occlusive layer from the second carrier film prior to irradiation.

29. A medical skin covering composition comprising a mixture comprising curable molecules that are curable by free radical polymerization, a photoinitiator, and a stabiliser, wherein the curable molecules are oligomers of at least one of the following formulae (I) to (VII):

$$CA(BA)_nC \qquad (I)$$

where n is 0 or an integer from 1 to 100,
A is a diisocyanate, a diepoxide, a diol or a dicarboxylic acid;
B is a diol when A is a diisocyanate or a dicarboxylic acid; B is a dicarboxylic acid when A is a diepoxide or a diol;
C is a hydroxyl containing methacrylate ester when A is a diisocyanate or a dicarboxylic acid; C is methacrylic acid when A is a diepoxide or a diol;

$$C_2E(BCE)_nC \qquad (II)$$

where n is 0 or an integer from 1 to 100,
E is a tri-isocyanate, a triepoxide, a triol or a tricarboxylic acid;
B is a diol when E is a tri-isocyanate or a tricarboxylic acid; B is a dicarboxylic acid when E is a triepoxide or a triol;
C is a hydroxyl containing methacrylate ester when E is a triisocyanate or a tricarboxylic acid; C is methacrylic acid when E is a triepoxide or a triol;

$$E_{(2n+1)}F_nC_{(3n+3)} \qquad (III)$$

where n is 0 or an integer from 1 to 100,
E is a tri-isocyanate, a triepoxide, a triol or a tricarboxylic acid;
F is a triol when E is a tri-isocyanate or a tricarboxylic acid; F is a tricarboxylic acid when E is a triepoxide or a triol;
C is a hydroxyl containing methacrylate ester when E is a triisocyanate or a tricarboxylic acid; C is methacrylic acid when E is a triepoxide or a triol;

$$G_{(n+1)}B_nC_{(2n+4)} \qquad (IV)$$

where n is 0 or an integer from 1 to 100,
G is a tetra-isocyanate or a tetra-carboxylic acid;
B is a diol;
C is a hydroxyl containing methacrylate ester;

$$DC_3 \tag{V}$$

where D is a symmetrical isocyanurate trimeric ring structure or an asymmetric trimeric iminooxadiazinedione ring structure consisting of three diisocyanate molecules, or a linear trimeric biuret or allophanate structure,
C is a hydroxyl containing methacrylate ester;

$$H_xC_{(x+2)} \tag{VI}$$

where x is 1, 2, 3, 4, 5 or 6,
$H_x$ is x symmetrical isocyanurate trimeric ring structures or x asymmetric trimeric iminooxadiazinedione ring structures consisting of three diisocyanate molecules, or x linear trimeric biuret or allophanate structures linked together in a homopolymer,
C is a hydroxyl containing methacrylate ester;

$$I_yC_y \tag{VII}$$

where y is 2, 3, 4, 5, 6, 7, 8, or 9,
$I_y$ is polyisocyanate, a polyepoxide, a polyol or a polycarboxylic acid with y numbers of functionalities;
C is a hydroxyl containing methacrylate ester when I is a polyisocyanate or a polycarboxylic acid; C is methacrylic acid when I is a polyepoxide or a polyol;
wherein the oligomers have a weight average molecular weight in the range from 1,500 to 10,000 dalton and wherein the composition is transformable from a viscoelastic state to an elastic state upon exposure to UV light or visible light.

30. The medical skin covering composition of claim 29, comprising a mixture, in proportions by weight based on the weight of the composition, of:
90% to 99.5% of said curable molecules curable by free radical polymerization;
0.05% to 10% of photoinitiator, and
0.1% to 0.5% of stabiliser.

31. The medical skin covering composition of claim 29, wherein the composition further contains up to 10% by weight of an adhesive component, the weight proportion of the adhesive component being calculated on the basis of its dry weight.

32. The medical skin covering composition of claim 31, wherein the adhesive component and the curable molecules are mutually soluble when dry.

33. The medical skin covering composition of claim 31, wherein the adhesive component is a mixture.

34. The medical skin covering composition of claim 29, wherein the photoinitiator is selected from the group consisting of benzoin ethyl ether, ethanone, 1-[9-ethyl-6-(2-methylbenzoyl)-9H-carbazol-3-yl]-1-(O-acetyl oxime), 2-benzyl-2-dimethylamino-1-(4-morpholinophenyl)-butanone-1, Bis(2,4,6-trimethylbenzoyl)-phenylphosphineoxide, 2,4,6-trimethylbenzoyldiphenylphosphine oxide, 2-ethyl anthraquinone, 2-methyl-1[4-(methylthio)phenyl]-2-morpholino propan-1-one; titanocene photoinitiators; dye/co-initiator systems including thionine/triethanolamine; dye/borate salt systems; dye/peroxide systems and 1,2-diketone/co-initiator systems, including camphor-quinone/tertiary amine and diethylthioxanthone/tertiary amine.

35. The medical skin covering composition of claim 29, wherein the photoinitiator is reactive to visible light.

36. A method of applying a surgical incision drape to an intended incision site on a patient's skin using a medical skin covering composition comprising a mixture comprising curable molecules that are curable by free radical polymerization, a photoinitiator, and a stabiliser, the method comprising:
(i) applying the composition and spreading it over the intended site of the incision; and
(ii) subjecting the composition spread over the intended site of the incision to visible light or UV irradiation to effect cure of the curable molecules in the composition;
wherein the curable molecules are oligomers of at least one of the following formulae (I) to (VII):

$$CA(BA)_nC \tag{I}$$

where n is 0 or an integer from 1 to 100,
A is a diisocyanate, a diepoxide, a diol or a dicarboxylic acid;
B is a diol when A is a diisocyanate or a dicarboxylic acid; B is a dicarboxylic acid when A is a diepoxide or a diol;
C is a hydroxyl containing methacrylate ester when A is a diisocyanate or a dicarboxylic acid; C is methacrylic acid when A is a diepoxide or a diol;

$$C_2E(BCE)_nC \tag{II}$$

where n is 0 or an integer from 1 to 100,
E is a tri-isocyanate, a triepoxide, a triol or a tricarboxylic acid;
B is a diol when E is a tri-isocyanate or a tricarboxylic acid; B is a dicarboxylic acid when E is a triepoxide or a triol;
C is a hydroxyl containing methacrylate ester when E is a triisocyanate or a tricarboxylic acid; C is methacrylic acid when E is a triepoxide or a triol;

$$E_{(2n+1)}F_nC_{(3n+3)} \tag{III}$$

where n is 0 or an integer from 1 to 100,
E is a tri-isocyanate, a triepoxide, a triol or a tricarboxylic acid;
F is a triol when E is a tri-isocyanate or a tricarboxylic acid; F is a tricarboxylic acid when E is a triepoxide or a triol;
C is a hydroxyl containing methacrylate ester when E is a triisocyanate or a tricarboxylic acid; C is methacrylic acid when E is a triepoxide or a triol;

$$G_{(n+1)}B_nC_{(2n+4)} \tag{IV}$$

where n is 0 or an integer from 1 to 100,
G is a tetra-isocyanate or a tetra-carboxylic acid;
B is a diol;
C is a hydroxyl containing methacrylate ester;

$$DC_3 \tag{V}$$

where D is a symmetrical isocyanurate trimeric ring structure or an asymmetric trimeric iminooxadiazinedione ring structure consisting of three diisocyanate molecules, or a linear trimeric biuret or allophanate structure,
C is a hydroxyl containing methacrylate ester;

$$H_xC_{(x+2)} \tag{VI}$$

where x is 1, 2, 3, 4, 5 or 6,
$H_x$ is x symmetrical isocyanurate trimeric ring structures or x asymmetric trimeric iminooxadiazinedione ring structures consisting of three diisocyanate molecules, or x linear trimeric biuret or allophanate structures linked together in a homopolymer, C is a hydroxyl containing methacrylate ester;

$$I_y C_y \qquad (VII)$$

where y is 2, 3, 4, 5, 6, 7, 8, or 9, $I_y$ is polyisocyanate, a polyepoxide, a polyol or a polycarboxylic acid with y numbers of functionalities;

C is a hydroxyl containing methacrylate ester when I is a polyisocyanate or a polycarboxylic acid; C is methacrylic acid when I is a polyepoxide or a polyol;

wherein the oligomers have a weight average molecular weight in the range from 1,500 to 10,000 dalton.

37. A method of applying a bacterial barrier to a wound on a patient's skin using a medical skin covering composition comprising a mixture comprising curable molecules that are curable by free radical polymerization, a photoinitiator, and a stabiliser, the method comprising:
  (i) applying the composition and spreading it over the site of the wound; and
  (ii) subjecting the composition spread over the site of the wound to visible light or UV irradiation to effect cure of the curable molecules in the composition;
  wherein the curable molecules are oligomers of at least one of the following formulae (I) to (VII):

$$CA(BA)_n C \qquad (I)$$

where n is 0 or an integer from 1 to 100,

A is a diisocyanate, a diepoxide, a diol or a dicarboxylic acid;

B is a diol when A is a diisocyanate or a dicarboxylic acid; B is a dicarboxylic acid when A is a diepoxide or a diol;

C is a hydroxyl containing methacrylate ester when A is a diisocyanate or a dicarboxylic acid; C is methacrylic acid when A is a diepoxide or a diol;

$$C_2 E(BCE)_n C \qquad (II)$$

where n is 0 or an integer from 1 to 100,

E is a tri-isocyanate, a triepoxide, a triol or a tricarboxylic acid;

B is a diol when E is a tri-isocyanate or a tricarboxylic acid; B is a dicarboxylic acid when E is a triepoxide or a triol;

C is a hydroxyl containing methacrylate ester when E is a triisocyanate or a tricarboxylic acid; C is methacrylic acid when E is a triepoxide or a triol;

$$E_{(2n+1)} F_n C_{(3n+3)} \qquad (III)$$

where n is 0 or an integer from 1 to 100,

E is a tri-isocyanate, a triepoxide, a triol or a tricarboxylic acid;

F is a triol when E is a tri-isocyanate or a tricarboxylic acid; F is a tricarboxylic acid when E is a triepoxide or a triol;

C is a hydroxyl containing methacrylate ester when E is a triisocyanate or a tricarboxylic acid; C is methacrylic acid when E is a triepoxide or a triol;

$$G_{(n+1)} B_n C_{(2n+4)} \qquad (IV)$$

where n is 0 or an integer from 1 to 100,

G is a tetra-isocyanate or a tetra-carboxylic acid;

B is a diol;

C is a hydroxyl containing methacrylate ester;

$$DC_3 \qquad (V)$$

where D is a symmetrical isocyanurate trimeric ring structure or an asymmetric trimeric iminooxadiazinedione ring structure consisting of three diisocyanate molecules, or a linear trimeric biuret or allophanate structure, C is a hydroxyl containing methacrylate ester;

$$H_x C_{(x+2)} \qquad (VI)$$

where x is 1, 2, 3, 4, 5 or 6, $H_x$ is x symmetrical isocyanurate trimeric ring structures or x asymmetric trimeric iminooxadiazinedione ring structures consisting of three diisocyanate molecules, or x linear trimeric biuret or allophanate structures linked together in a homopolymer, C is a hydroxyl containing methacrylate ester;

$$I_y C_y \qquad (VII)$$

where y is 2, 3, 4, 5, 6, 7, 8, or 9, $I_y$ is polyisocyanate, a polyepoxide, a polyol or a polycarboxylic acid with y numbers of functionalities;

C is a hydroxyl containing methacrylate ester when I is a polyisocyanate or a polycarboxylic acid; C is methacrylic acid when I is a polyepoxide or a polyol;

wherein the oligomers have a weight average molecular weight in the range from 1,500 to 10,000 dalton.

38. A method of closing the edges of a wound using a medical skin covering composition comprising a mixture comprising curable molecules that are curable by free radical polymerization, a photoinitiator, and a stabiliser, the method comprising:
  (i) bringing the edges of the wound together and applying the composition and spreading it over the site of the wound; and
  (ii) subjecting the composition spread over the wound to visible light or UV irradiation to effect cure of the curable molecules in the composition;
  wherein the curable molecules are oligomers of at least one of the following formulae (I) to (VII):

$$CA(BA)_n C \qquad (I)$$

where n is 0 or an integer from 1 to 100,

A is a diisocyanate, a diepoxide, a diol or a dicarboxylic acid;

B is a diol when A is a diisocyanate or a dicarboxylic acid; B is a dicarboxylic acid when A is a diepoxide or a diol;

C is a hydroxyl containing methacrylate ester when A is a diisocyanate or a dicarboxylic acid; C is methacrylic acid when A is a diepoxide or a diol;

$$C_2 E(BCE)_n C \qquad (II)$$

where n is 0 or an integer from 1 to 100,

E is a tri-isocyanate, a triepoxide, a triol or a tricarboxylic acid;

B is a diol when E is a tri-isocyanate or a tricarboxylic acid; B is a dicarboxylic acid when E is a triepoxide or a triol;

C is a hydroxyl containing methacrylate ester when E is a triisocyanate or a tricarboxylic acid; C is methacrylic acid when E is a triepoxide or a triol;

$$E_{(2n+1)} F_n C_{(3n+3)} \qquad (III)$$

where n is 0 or an integer from 1 to 100,

E is a tri-isocyanate, a triepoxide, a triol or a tricarboxylic acid;

F is a triol when E is a tri-isocyanate or a tricarboxylic acid; F is a tricarboxylic acid when E is a triepoxide or a triol;

C is a hydroxyl containing methacrylate ester when E is a triisocyanate or a tricarboxylic acid; C is methacrylic acid when E is a triepoxide or a triol;

$$G_{(n+1)}B_nC_{(2n+4)} \qquad (IV)$$

where n is 0 or an integer from 1 to 100,
G is a tetra-isocyanate or a tetra-carboxylic acid;
B is a diol;
C is a hydroxyl containing methacrylate ester;

$$DC_3 \qquad (V)$$

where D is a symmetrical isocyanurate trimeric ring structure or an asymmetric trimeric iminooxadiazinedione ring structure consisting of three diisocyanate molecules, or a linear trimeric biuret or allophanate structure,
C is a hydroxyl containing methacrylate ester;

$$H_xC_{(x+2)} \qquad (VI)$$

where x is 1, 2, 3, 4, 5 or 6,
$H_x$ is x symmetrical isocyanurate trimeric ring structures or x asymmetric trimeric iminooxadiazinedione ring structures consisting of three diisocyanate molecules, or x linear trimeric biuret or allophanate structures linked together in a homopolymer,
C is a hydroxyl containing methacrylate ester;

$$I_yC_y \qquad (VII)$$

where y is 2, 3, 4, 5, 6, 7, 8, or 9,
$I_y$ is polyisocyanate, a polyepoxide, a polyol or a polycarboxylic acid with y numbers of functionalities;
C is a hydroxyl containing methacrylate ester when I is a polyisocyanate or a polycarboxylic acid; C is methacrylic acid when I is a polyepoxide or a polyol;
wherein the oligomers have a weight average molecular weight in the range from 1,500 to 10,000 dalton.

* * * * *